US012778763B2

(12) United States Patent
Desens et al.

(10) Patent No.: US 12,778,763 B2
(45) Date of Patent: Nov. 3, 2026

(54) INSERTION AND REMOVAL FEATURES FOR MODULAR STEMS AND ASSOCIATED METHODS

(71) Applicant: WRIGHT MEDICAL TECHNOLOGY, INC., Memphis, TN (US)

(72) Inventors: Collin Desens, Hoboken, NJ (US); Meghan Kubacki, Memphis, TN (US); James Edward Smith, Jr., Arlington, TN (US); Kevin Froster, Marlboro, NJ (US)

(73) Assignee: WRIGHT MEDICAL TECHNOLOGY, INC., Memphis, TN (US)

(*) Notice: Subject to any disclaimer, the term of this patent is extended or adjusted under 35 U.S.C. 154(b) by 943 days.

(21) Appl. No.: 18/065,050

(22) Filed: Dec. 13, 2022

(65) Prior Publication Data

US 2023/0285158 A1 Sep. 14, 2023

Related U.S. Application Data

(60) Provisional application No. 63/269,269, filed on Mar. 14, 2022.

(51) Int. Cl.
*A61F 2/42* (2006.01)
*A61F 2/30* (2006.01)
(Continued)

(52) U.S. Cl.
CPC .......... *A61F 2/4202* (2013.01); *A61F 2/3094* (2013.01); *A61F 2/4684* (2013.01); (Continued)

(58) Field of Classification Search
CPC ................................ F16B 7/00; A61F 2/4202; A61F 2002/30607; A61F 2002/4638; A61F 2002/30332; A61F 2002/30405
See application file for complete search history.

(56) References Cited

U.S. PATENT DOCUMENTS 3,839,742 A 10/1974 Link
3,872,519 A 3/1975 Giannestras et al.
(Continued)

FOREIGN PATENT DOCUMENTS

CA 2836651 3/2016
CN 101790353 7/2010
(Continued)

OTHER PUBLICATIONS

Renz EP 3 786 465 A1 with English Translation (Year: 2019).*
(Continued)

*Primary Examiner* — Marcia L Watkins
(74) *Attorney, Agent, or Firm* — DUANE MORRIS LLP

(57) ABSTRACT

An apparatus may include a body extending from a first end to a second end. The first end of the body may include a first coupling element, and the second end of the body may include a second coupling element. The second end of the body may include a first engagement element that extends inwardly into the body and may be disposed between a peripheral edge of the body and the second coupling element. Methods are also disclosed.

36 Claims, 28 Drawing Sheets

(51) Int. Cl.
*A61F 2/46* (2006.01)
*B33Y 80/00* (2015.01)
*F16B 7/00* (2006.01)

(52) U.S. Cl.
CPC ............... *A61F 2002/30224* (2013.01); *A61F 2002/30273* (2013.01); *A61F 2002/30276* (2013.01); *A61F 2002/30383* (2013.01); *A61F 2002/30405* (2013.01); *A61F 2002/30604* (2013.01); *A61F 2002/4205* (2013.01); *B33Y 80/00* (2014.12); *F16B 7/00* (2013.01)

(56) References Cited

U.S. PATENT DOCUMENTS 3,886,599 A 6/1975 Schlein
3,889,300 A 6/1975 Smith
3,896,502 A 7/1975 Lennox
3,896,503 A 7/1975 Freeman et al.
3,975,778 A 8/1976 Newton, III
3,987,500 A 10/1976 Schlein
4,021,864 A 5/1977 Waugh
4,069,518 A 1/1978 Groth, Jr. et al.
4,156,944 A 6/1979 Schreiber et al.
4,166,292 A 9/1979 Bokros
4,204,284 A 5/1980 Koeneman
4,232,404 A 11/1980 Samuelson et al.
4,309,778 A 1/1982 Buechel et al.
4,470,158 A 9/1984 Pappas et al.
4,755,185 A 7/1988 Tarr
4,968,316 A 11/1990 Hergenroeder
5,041,139 A 8/1991 Brånemark
5,312,412 A 5/1994 Whipple
5,326,365 A 7/1994 Alvine
5,354,300 A 10/1994 Goble et al.
5,358,526 A 10/1994 Tornier
5,395,188 A 3/1995 Bailey et al.
5,423,825 A 6/1995 Levine
5,476,466 A 12/1995 Barrette et al.
5,507,818 A 4/1996 McLaughlin
5,601,563 A 2/1997 Burke et al.
5,628,749 A 5/1997 Vendrely et al.
5,634,927 A 6/1997 Houston et al.
5,667,511 A 9/1997 Vendrely et al.
5,674,223 A 10/1997 Cipolletti et al.
5,735,904 A 4/1998 Pappas
5,766,259 A 6/1998 Sammarco
5,776,200 A 7/1998 Johnson et al.
5,817,097 A 10/1998 Howard et al.
5,824,106 A 10/1998 Fournal
5,879,389 A 3/1999 Koshino
5,885,299 A 3/1999 Winslow et al.
5,888,203 A 3/1999 Goldberg
5,897,559 A 4/1999 Masini
5,935,132 A 8/1999 Bettuchi et al.
6,002,859 A 12/1999 DiGioia, III et al.
6,033,405 A 3/2000 Winslow et al.
6,053,922 A 4/2000 Krause et al.
6,102,952 A 8/2000 Koshino
6,183,519 B1 2/2001 Bonnin et al.
6,214,052 B1 4/2001 Burkinshaw
6,245,109 B1 6/2001 Mendes et al.
6,342,056 B1 1/2002 Mac-Thiong et al.
6,344,043 B1 2/2002 Pappas
6,409,767 B1 6/2002 Pericé et al.
6,436,146 B1 8/2002 Hassler et al.
6,478,800 B1 11/2002 Fraser et al.
6,520,964 B2 2/2003 Tallarida et al.
6,530,930 B1 3/2003 Marino et al.
6,602,259 B1 8/2003 Masini
6,610,067 B2 8/2003 Tallarida et al.
6,610,095 B1 8/2003 Pope et al.
6,620,168 B1 9/2003 Lombardo et al.
6,645,215 B1 11/2003 McGovern et al.
6,663,669 B1 12/2003 Reiley
6,673,116 B2 1/2004 Reiley
6,679,917 B2 1/2004 Ek
6,719,799 B1 4/2004 Kropf
6,824,567 B2 11/2004 Tornier et al.
6,852,130 B2 2/2005 Keller et al.
6,860,902 B2 3/2005 Reiley
6,863,691 B2 3/2005 Short et al.
6,875,222 B2 4/2005 Long et al.
6,875,236 B2 4/2005 Reiley
6,926,739 B1 8/2005 O'Connor et al.
6,939,380 B2 9/2005 Guzman
6,942,670 B2 9/2005 Heldreth et al.
6,964,663 B2 11/2005 Grant et al.
7,001,394 B2 2/2006 Gundlapalli et al.
7,011,687 B2 3/2006 Deffenbaugh et al.
7,025,790 B2 4/2006 Parks et al.
7,163,541 B2 1/2007 Ek
7,238,190 B2 7/2007 Schon et al.
7,252,684 B2 8/2007 Dearnaley
7,314,488 B2 1/2008 Reiley
7,323,012 B1 1/2008 Stone et al.
7,476,227 B2 1/2009 Tornier et al.
7,481,814 B1 1/2009 Metzger
7,485,147 B2 2/2009 Papps et al.
7,534,246 B2 5/2009 Reiley et al.
7,534,270 B2 5/2009 Ball
7,615,082 B2 11/2009 Naegerl et al.
7,618,421 B2 11/2009 Axelson, Jr. et al.
7,625,409 B2 12/2009 Saltzman et al.
7,641,697 B2 1/2010 Reiley
7,678,151 B2 3/2010 Ek
7,713,305 B2 5/2010 Ek
7,717,920 B2 5/2010 Reiley
7,763,080 B2 7/2010 Southworth
7,803,158 B2 9/2010 Hayden
7,850,698 B2 12/2010 Straszheim-Morley et al.
7,896,883 B2 3/2011 Ek et al.
7,896,885 B2 3/2011 Miniaci et al.
7,909,882 B2 3/2011 Stinnette
7,914,533 B2 3/2011 Nelson et al.
7,963,996 B2 6/2011 Saltzman et al.
8,002,841 B2 8/2011 Hasselman
8,012,217 B2 9/2011 Strzepa et al.
8,034,114 B2 10/2011 Reiley
8,034,115 B2 10/2011 Reiley
8,048,164 B2 11/2011 Reiley
8,110,006 B2 2/2012 Reiley
8,114,091 B2 2/2012 Ratron et al.
8,128,627 B2 3/2012 Justin et al.
8,167,888 B2 5/2012 Steffensmeier
8,172,850 B2 5/2012 McMinn
8,177,841 B2 5/2012 Ek
8,192,434 B2 6/2012 Huebner et al.
8,268,007 B2 9/2012 Barsoum et al.
8,303,667 B2 11/2012 Younger
8,313,492 B2 11/2012 Wong et al.
8,317,797 B2 11/2012 Rasmussen
8,323,346 B2 12/2012 Tepic
8,337,503 B2 12/2012 Lian
8,361,159 B2 1/2013 Ek
8,366,559 B2 2/2013 Papenfuss et al.
8,430,879 B2 4/2013 Stoneburner et al.
8,475,463 B2 7/2013 Lian
8,491,596 B2 7/2013 Long et al.
8,579,980 B2 11/2013 DeLurio et al.
8,715,362 B2 5/2014 Reiley et al.
8,808,303 B2 8/2014 Stemniski et al.
8,911,444 B2 12/2014 Bailey
9,259,250 B2 2/2016 Saravia et al.
9,480,571 B2 11/2016 McGinley et al.
9,492,281 B2 11/2016 Rouyer et al.
9,629,726 B2 4/2017 Reiley et al.
9,629,730 B2 4/2017 Reiley
9,907,561 B2 3/2018 Luna et al.
10,034,678 B2 7/2018 Park et al.
10,039,558 B2 8/2018 Park et al.
10,111,674 B2 10/2018 Crainich et al.
10,136,904 B2 11/2018 McGinley et al.
10,149,687 B2 12/2018 McGinley et al.
10,182,832 B1 1/2019 Saltzman et al.

(56) References Cited

U.S. PATENT DOCUMENTS

| | | | |
|---|---|---|---|
| 10,206,688 | B2 | 2/2019 | Park et al. |
| 10,743,999 | B2 | 8/2020 | Reiley |
| 10,940,012 | B2 | 3/2021 | Sander et al. |
| 11,013,520 | B2 | 5/2021 | Gareiss et al. |
| 2002/0068977 | A1 | 6/2002 | Jackson |
| 2002/0082607 | A1 | 6/2002 | Heldreth et al. |
| 2002/0133164 | A1 | 9/2002 | Williamson |
| 2002/0173853 | A1 | 11/2002 | Corl, III et al. |
| 2003/0208280 | A1 | 11/2003 | Tohidi |
| 2003/0236522 | A1 | 12/2003 | Long et al. |
| 2004/0030399 | A1 | 2/2004 | Asencio |
| 2004/0039394 | A1 | 2/2004 | Conti et al. |
| 2004/0068322 | A1 | 4/2004 | Ferree |
| 2004/0167631 | A1 | 8/2004 | Luchesi et al. |
| 2004/0186585 | A1 | 9/2004 | Feiwell |
| 2004/0193268 | A1 | 9/2004 | Hazebrouck |
| 2004/0216259 | A1 | 11/2004 | Ponziani |
| 2004/0236431 | A1 | 11/2004 | Sekel |
| 2005/0004676 | A1 | 1/2005 | Schon et al. |
| 2005/0165408 | A1 | 7/2005 | Puno et al. |
| 2005/0192674 | A1 | 9/2005 | Ferree |
| 2005/0267481 | A1 | 12/2005 | Carl et al. |
| 2006/0009857 | A1 | 1/2006 | Gibbs et al. |
| 2006/0020345 | A1 | 1/2006 | O'Connor et al. |
| 2006/0036257 | A1 | 2/2006 | Steffensmeier et al. |
| 2006/0116679 | A1 | 6/2006 | Lutz et al. |
| 2006/0142870 | A1 | 6/2006 | Robinson et al. |
| 2006/0229730 | A1 | 10/2006 | Railey et al. |
| 2006/0235541 | A1 | 10/2006 | Hodorek |
| 2006/0247788 | A1 | 11/2006 | Ross |
| 2007/0038303 | A1 | 2/2007 | Myerson et al. |
| 2007/0100346 | A1 | 5/2007 | Wyss et al. |
| 2007/0112431 | A1 | 5/2007 | Kofoed |
| 2007/0162025 | A1 | 7/2007 | Tornier et al. |
| 2007/0173944 | A1 | 7/2007 | Keller et al. |
| 2007/0173947 | A1 | 7/2007 | Ratron |
| 2007/0213830 | A1 | 9/2007 | Ammann et al. |
| 2007/0233129 | A1 | 10/2007 | Bertagnoli et al. |
| 2007/0276400 | A1 | 11/2007 | Moore et al. |
| 2007/0288030 | A1 | 12/2007 | Metzger et al. |
| 2008/0015602 | A1 | 1/2008 | Axelson |
| 2008/0097617 | A1 | 4/2008 | Fellinger et al. |
| 2008/0103603 | A1 | 5/2008 | Hintermann |
| 2008/0109081 | A1 | 5/2008 | Bao et al. |
| 2008/0195233 | A1 | 8/2008 | Ferrari et al. |
| 2008/0215156 | A1 | 9/2008 | Duggal et al. |
| 2008/0287954 | A1 | 11/2008 | Kunz et al. |
| 2008/0312745 | A1 | 12/2008 | Keller et al. |
| 2009/0024131 | A1 | 1/2009 | Metzger et al. |
| 2009/0043309 | A1 | 2/2009 | Rasmussen |
| 2009/0043310 | A1 | 2/2009 | Rasmussen |
| 2009/0054992 | A1 | 2/2009 | Landes et al. |
| 2009/0082875 | A1 | 3/2009 | Long |
| 2009/0105767 | A1 | 4/2009 | Reiley |
| 2009/0105840 | A1 | 4/2009 | Reiley |
| 2009/0182433 | A1 | 7/2009 | Reiley et al. |
| 2009/0198341 | A1 | 8/2009 | Choi et al. |
| 2009/0234360 | A1 | 9/2009 | Alexander |
| 2009/0276052 | A1 | 11/2009 | Regala et al. |
| 2010/0010493 | A1 | 1/2010 | Dower |
| 2010/0023066 | A1 | 1/2010 | Long et al. |
| 2010/0023126 | A1 | 1/2010 | Grotz |
| 2010/0057216 | A1 | 3/2010 | Gannoe et al. |
| 2010/0069910 | A1 | 3/2010 | Hasselman |
| 2010/0198355 | A1 | 8/2010 | Kofoed et al. |
| 2010/0212138 | A1 | 8/2010 | Carroll et al. |
| 2010/0241237 | A1 | 9/2010 | Pappas |
| 2010/0262150 | A1 | 10/2010 | Lian |
| 2010/0305572 | A1 | 12/2010 | Saltzman et al. |
| 2010/0318088 | A1 | 12/2010 | Warne et al. |
| 2010/0331984 | A1 | 12/2010 | Barsoum et al. |
| 2011/0029090 | A1 | 2/2011 | Zannis et al. |
| 2011/0035018 | A1 | 2/2011 | Deffenbaugh et al. |
| 2011/0035019 | A1 | 2/2011 | Goswami et al. |
| 2011/0071645 | A1 | 3/2011 | Bojarski et al. |
| 2011/0106268 | A1 | 5/2011 | Deffenbaugh et al. |
| 2011/0112542 | A1 | 5/2011 | Gross |
| 2011/0125200 | A1 | 5/2011 | Hanson et al. |
| 2011/0125275 | A1 | 5/2011 | Lipman et al. |
| 2011/0125284 | A1 | 5/2011 | Gabbrielli et al. |
| 2011/0152868 | A1 | 6/2011 | Kourtis et al. |
| 2011/0152869 | A1 | 6/2011 | Ek et al. |
| 2011/0166608 | A1 | 7/2011 | Duggal et al. |
| 2011/0190829 | A1 | 8/2011 | Duggal et al. |
| 2011/0218542 | A1 | 9/2011 | Lian |
| 2011/0245835 | A1 | 10/2011 | Dodd et al. |
| 2011/0253151 | A1 | 10/2011 | Tochigi et al. |
| 2011/0276052 | A1 | 11/2011 | Hasselman |
| 2011/0295380 | A1 | 12/2011 | Long |
| 2012/0010718 | A1 | 1/2012 | Still |
| 2012/0046753 | A1 | 2/2012 | Cook et al. |
| 2012/0053591 | A1 | 3/2012 | Haines et al. |
| 2012/0053644 | A1 | 3/2012 | Landry et al. |
| 2012/0083789 | A1 | 4/2012 | Blakemore et al. |
| 2012/0109131 | A1 | 5/2012 | Vasarhelyi et al. |
| 2012/0109326 | A1 | 5/2012 | Perler |
| 2012/0130376 | A1 | 5/2012 | Loring et al. |
| 2012/0136443 | A1 | 5/2012 | Wenzel |
| 2012/0185057 | A1 | 7/2012 | Abidi et al. |
| 2012/0191210 | A1 | 7/2012 | Ratron et al. |
| 2012/0239045 | A1 | 9/2012 | Li |
| 2012/0245701 | A1 | 9/2012 | Zak et al. |
| 2012/0271314 | A1 | 10/2012 | Stemniski et al. |
| 2012/0271430 | A1 | 10/2012 | Arnett et al. |
| 2012/0277745 | A1 | 11/2012 | Lizee |
| 2013/0041473 | A1 | 2/2013 | Rouyer et al. |
| 2013/0116797 | A1 | 5/2013 | Coulange et al. |
| 2014/0020690 | A1 | 1/2014 | Triplett |
| 2014/0236157 | A1 | 8/2014 | Tochigi et al. |
| 2014/0276853 | A1 | 9/2014 | Long et al. |
| 2014/0296995 | A1 | 10/2014 | Reiley et al. |
| 2014/0309640 | A1 | 10/2014 | Smith et al. |
| 2014/0336658 | A1 | 11/2014 | Luna et al. |
| 2015/0045801 | A1 | 2/2015 | Axelson et al. |
| 2015/0314429 | A1* | 11/2015 | Doroslovac ........... B25B 13/065 81/441 |
| 2016/0135815 | A1 | 5/2016 | Loring et al. |
| 2016/0135857 | A1 | 5/2016 | Marrero, Sr. |
| 2016/0361071 | A1 | 12/2016 | Mahfouz |
| 2017/0189198 | A1 | 7/2017 | Reiley et al. |
| 2018/0177511 | A1 | 6/2018 | Luna et al. |
| 2018/0263639 | A1 | 9/2018 | McGinley et al. |
| 2019/0059917 | A1 | 2/2019 | Saltzman |
| 2019/0059918 | A1 | 2/2019 | Saltzman et al. |
| 2019/0133612 | A1 | 5/2019 | McGinley |
| 2022/0316504 | A1 | 10/2022 | Kubacki |

FOREIGN PATENT DOCUMENTS

| | | | | |
|---|---|---|---|---|
| DE | 33 19916 | A1 * | 12/1984 | ........... A61F 2/4637 |
| DE | 69221843 | | 10/1997 | |
| EP | 2967697 | | 4/2018 | |
| EP | 3354233 | | 10/2019 | |
| EP | 3785671 | A1 | 3/2021 | |
| EP | 3786465 | A1 * | 3/2021 | .......... F16B 25/0094 |
| GB | 2480846 | | 12/2011 | |
| JP | H11-500035 | | 1/1999 | |
| JP | 2006150055 | | 6/2006 | |
| JP | 2007508123 | | 4/2007 | |
| JP | 2007518453 | | 7/2007 | |
| JP | 2007519477 | | 7/2007 | |
| JP | 2007536011 | | 12/2007 | |
| JP | 2009148597 | | 7/2009 | |
| JP | 2011526189 | | 10/2011 | |
| JP | 2012518517 | | 8/2012 | |
| JP | 2013500810 | | 1/2013 | |
| JP | 2013511358 | | 4/2013 | |
| JP | 5412334 | | 2/2014 | |
| JP | 2014131738 | | 7/2014 | |
| WO | WO 9625106 | | 8/1996 | |
| WO | WO 0166021 | A1 | 9/2001 | |
| WO | WO 2005011523 | A2 | 2/2005 | |
| WO | WO 2005037135 | | 4/2005 | |
| WO | WO 2006022923 | | 3/2006 | |

(56) References Cited

FOREIGN PATENT DOCUMENTS

| | | | |
|---|---|---|---|
| WO | WO 2006023824 | | 3/2006 |
| WO | WO 2006099270 | | 9/2006 |
| WO | WO 2007084846 | | 7/2007 |
| WO | WO 2009143374 | | 11/2009 |
| WO | WO 2009158522 | | 12/2009 |
| WO | WO 2010099142 | | 9/2010 |
| WO | WO 2010135156 | | 11/2010 |
| WO | WO 2011015863 | | 2/2011 |
| WO | WO 2011063281 | | 5/2011 |
| WO | 2011103851 | A1 | 9/2011 |
| WO | WO 2011151657 | | 12/2011 |
| WO | WO 2012088036 | | 6/2012 |
| WO | WO 2012116089 | | 8/2012 |
| WO | WO 2012158917 | | 11/2012 |
| WO | WO 2013169475 | | 11/2013 |
| WO | WO 2014152535 | | 9/2014 |
| WO | WO 2015167581 | | 11/2015 |
| WO | WO 2016005722 | | 1/2016 |
| WO | WO 2016039762 | | 3/2016 |
| WO | 2016153658 | A1 | 9/2016 |
| WO | 2019125536 | A1 | 6/2019 |

OTHER PUBLICATIONS

Search report issued for European U.S. Appl. No. 13/198,280 dated Feb. 5, 2014.
International Search Report for International patent application No. PCT/US2014/027448 dated Jul. 7, 2014.
International Preliminary Report on Patentability issued for International patent application No. PCT/US2014/027448, Sep. 15, 2015, 8 pages.
Partial European Search Report issued in connection with European patent application No. 14768333.8, Oct. 26, 2016, 6 pages.
Patent Examination Report No. 1 issued in connection with Australian patent application No. 2015202080, Jul. 5, 2016, 4 pages.
First Office Action issued for Japanese patent application No. 2016-117842, Sep. 12, 2017, 5 pages.
First Office Action issued in connection with corresponding Japanese Patent Application No. 2020-016447, Apr. 6, 2021, 4 pages.
Office Action in corresponding Canadian Patent Application No. 2,904,652, Jun. 2, 2020, 6 pages.
First Examination Report issued in corresponding Australian Patent Application No. 2019213412, Sep. 3, 2020, 5 pages.
First Office Action in corresponding Canadian Patent Application No. 2,904,652, Jan. 28, 2020, 5 pages.
Final Office Action issued in connection with corresponding Japanese Patent Application No. 206-502443, May 15, 2018, 3 pages.
Extended European Search Report issued in connection with corresponding European Patent Application No. 18160378.8, Jun. 29, 2018, 7 pages.
Second Office Action issued in connection with corresponding Chinese Patent Application No. 2018071101785100, dated Jul. 16, 2016, 6 pages.
First Office Action in corresponding Japanese Patent Application No. 2018-178853, Sep. 3, 2018, 3 pages.
Examination Report No. 1 issued in connection with corresponding Australian Patent Application No. 20182000073, Dec. 24, 2018, 3 pages.
First Office Action issued in connection with corresponding Japanese Patent Application No. 2018-092289, Mar. 5, 2019, 2 pages.
Extended European Search Report and Opinion in connection with European Patent Application No. 14768333.8, dated Jan. 30, 2017, 10 pages.
First Office Action issued in connection with Chinese Patent Application No. 2017800899442 dated Apr. 6, 2022, 8 pages.
International Search Report and Written Opinion issued in connection with International Patent Application No. PCT/US2021/025873, Sep. 2, 2021.
Orthopedic Designs North America, Inc., http://odi-na.com/?service=talon-distalfix-fermoral-nail-system, accessed via Internet, Jul. 22, 2022.
Arthrex, "Arthrex—Intramedullary Nails," https://www.arthrex.com/foot-ankle/intramedullary-nails, accessed via Internet, Jul. 22, 2022.
Inbone II Total Ankle Surgical Technique, Wright Medical Technology, Inc., Mar. 12, 2014, 64 pages.
Infinity Total Ankle System Surgical Technique, Wright Medical Techology, Inc., Aug. 8, 2015, 76 pages.
First Examination Report issued in connection with Australian Patent Application No. 2020277219, Nov. 19, 2021, 7 pages.
International Search Report and Written Opinion issued in connection with International Patent Application No. PCT/US2016/023729, Feb. 14, 2017, 14 pages.
First Examination Report issued in connection with Australian Patent Application No. 2019246766, Apr. 17, 2020, 9 pages.
Supplementary European Search Report issued in connection with corresponding European Patent Application No. 16895669.6 Oct. 21, 2019, 6 pages.
Office Action in connection with corresponding Canadian Patent Application No. 3,014,284, Jun. 17, 2019, 4 pages.
First Examination issued in connection with Australian Patent Application No. 2016398429, Jan. 21, 2019, 4 pages.
Examination Report issued in connection with corresponding European Patent Application No. 22213919.8, Apr. 4, 2025, 8 pages.
Extended European Search Report issued in connection with European Patent Application No. 22213919.8, Aug. 3, 2023, 11 pages.

* cited by examiner

INSERTION AND REMOVAL FEATURES FOR MODULAR STEMS AND ASSOCIATED METHODS

CROSS-REFERENCE TO RELATED APPLICATION

This application claims priority under 35 U.S.C. § 119(e) to U.S. Provisional Application No. 63/269,269, filed on Mar. 14, 2022, the entire contents of which are incorporated herein by reference.

INCORPORATE BY REFERENCE

This application incorporates by reference the entireties of U.S. Pat. No. 8,715,362 and U.S. Provisional Patent Application No. 63/169,306, filed Apr. 1, 2021.

FIELD OF DISCLOSURE

The disclosed systems and methods relate to implants. More particularly, the disclosed systems and methods relate to the coupling and decoupling of two or more components of a prosthesis or implant.

BACKGROUND

Medical prostheses are available to address any number of abnormalities. For example, a prosthesis may be provided to replace a joint, such as a shoulder, elbow, knee, or ankle. Each prosthesis may include one or more components, such as a stem that is to be inserted into a passageway formed along an axis of a bone, and a tray that is to be coupled to the stem. A tray may support one or more additional components, such as an articular surface formed from metal or polymer that may be coupled to the tray. In order to speed recovery and reduce complications, surgical techniques seek to minimize the size or length of an incision or access site needed to install a prosthesis. As a result, there continues to be a need to minimize the size of the implant to be installed.

SUMMARY

In some embodiments, an apparatus may include a body extending from a first end to a second end. The first end of the body may include a first coupling element, and the second end of the body may include a second coupling element. The second end of the body may include a first engagement element that extends inwardly into the body and may be disposed between a peripheral edge of the body and the second coupling element.

In some embodiments, a system may include a prosthesis stem including a plurality of stem components. At least one stem component of the plurality of stem components may include a body extending from a first end to a second end. A first coupling element may be disposed at the first end of the body, and a second coupling element may be disposed at the second end of the body. At least one first engagement element may be disposed along a length of the body such that the at least one first engagement element may be disposed between the first end and the second end. A second engagement element may extend inwardly into the second end of the body. The second engagement element may surround the second coupling element such that the second engagement element may be disposed between the second coupling element and a peripheral edge of the body.

In some embodiments, a system may include a prosthesis stem. The prosthesis stem may include a plurality of stem components. A first stem component of the plurality of stem components may include a first body extending from a first end to a second end. A first coupling element may be disposed at the first end of the first body. A second coupling element may be disposed at the second end of the first body. A first engagement element may be accessible via the second end of the first body and may be disposed between the second coupling element and the first end of the first body. In some embodiments, a second engagement element may extend inwardly into the second end of the first body. The second engagement element may surround the second coupling element such that the second engagement element may be disposed between the second coupling element and a peripheral edge of the first body.

In some embodiments, a method may include engaging a first engagement element provided by a body of a first component and applying a torque to a body of a first component with the torquing instrument to couple the first component to a second component. The first engagement element may be disposed at a first end of the body of the first component and may extend inwardly into the body of the first component.

In some embodiments, a method may include inserting a male coupling element provided by a first component into a female coupling element provided by a second component, engaging a first engagement element with a torquing instrument, and applying a torque to the body of the first component with the torquing instrument to couple the first component to the second component. The first engagement element may be disposed at a first end of the body and may extend inwardly into a body of the first component.

In some embodiments, a method may include exposing at least a portion of a multi-component prosthesis stem that was previously implanted in a patient, inserting a torquing tool into a first engagement element of a plurality of engagement elements provided along a length of a first stem component of the multi-component prosthesis stem, and applying a first torque to a body of the first stem component of the multi-component stem to disengage a first coupling element of the first stem component from a first coupling element of a second component of the multi-component stem.

BRIEF DESCRIPTION OF THE DRAWINGS

The features and advantages of the present disclosures will be more fully disclosed in, or rendered obvious by the following detailed descriptions of example embodiments. The detailed descriptions of the example embodiments are to be considered together with the accompanying drawings wherein like numbers refer to like parts and further wherein.

DETAILED DESCRIPTION

Figure 2:
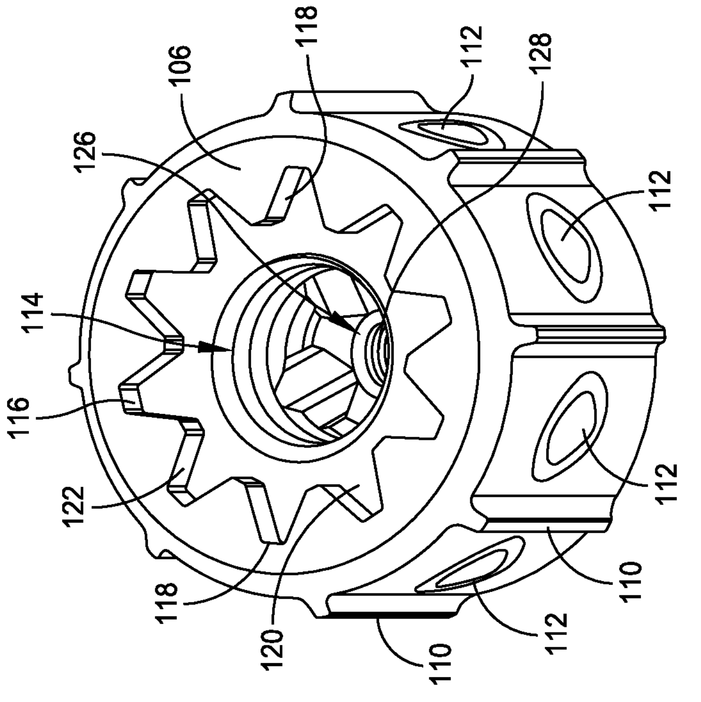
FIG. 2 is a bottom side isometric view of the stem component illustrated in FIG. 1, in accordance with some embodiments.

This description of the exemplary embodiments is intended to be read in connection with the accompanying drawings, which are to be considered part of the entire written description. The description of the preferred embodiments is intended to be read in connection with the accompanying drawings, which are to be considered part of the entire written description of these disclosures. While the present disclosure is susceptible to various modifications and alternative forms, specific embodiments are shown by way of example in the drawings and will be described in detail herein. The objectives and advantages of the claimed subject matter will become more apparent from the following detailed description of these exemplary embodiments in connection with the accompanying drawings.

The disclosed components, systems, and methods provide for coupling together two or more components of a medical prosthesis and facilitate the coupling together of the various components. The disclosed components, systems, and methods also provide for decoupling two or more components of a medical prosthesis to facilitate removal of the components. In some embodiments, the components may be coupled together in situ through a minimally invasive opening, although it should be understood that the components may be coupled together ex situ and implanted as a single construct. In some embodiments, two or more components may be assembled ex situ to form a first assembly, and at least one third component may be assembled to the first assembly in situ to form a second assembly. One or more fourth components may be assembled to the second assembly in situ. Although the following descriptions are provided with reference to an ankle prosthesis, such as the INBONE™ Total Ankle System available from the Wright Medical Group and the ankle prostheses disclosed in U.S. Pat. No. 8,715,362, entitled "Ankle Replacement System," which is incorporated by reference herein in its entirety, it should be understood that the disclosed systems and methods are not to be limited to such prosthesis and may be used in connection with any number of different prosthesis, including prostheses for joints other than ankles. For example, the disclosed components, systems, and methods may be applied to prosthesis for other joints including, but not limited, hips, shoulders, elbows, and knees, to list only a few possibilities.

Figure 1:
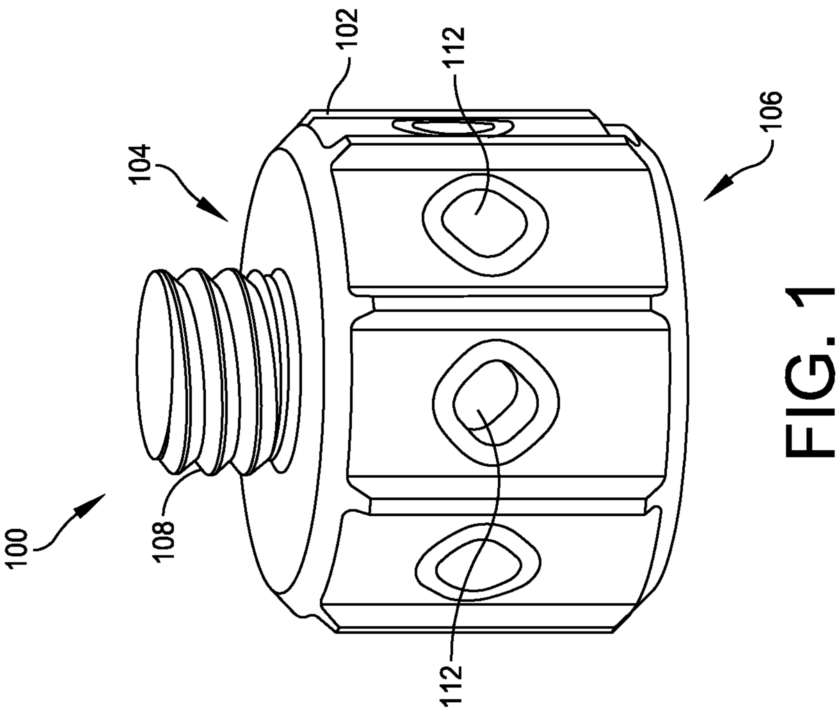
FIG. 1 is a top side isometric view of one example of a stem component, in accordance with some embodiments.

FIGS. 1-2 illustrate one example of a stem component 100 in accordance with some embodiments. In some embodiments, a system or kit may include a first prosthesis component 100 that may be coupled to another prosthesis component, such as another prosthesis stem component 100 and/or a tray, to list only a couple of possibilities. For example, the first prosthesis component 100 may be a stem component, such as a middle stem component, of a multi-component stem as disclosed in U.S. Pat. No. 8,715,362, which was incorporated by reference above, or a monolithic stem. The stem component 100 may include a body 102 having a generally cylindrical shape extending from a first end 104 to a second end 106, it should be understood that stem component 100 may have other shapes or configurations (e.g., conical, pyramidal, cubic, and/or oval, to list only a few examples). Body 102 may be formed using an additive manufacturing process, such as Direct Metal Laser Sintering (DMLS) or Electron Beam Melting (EBM), to list only a few possibilities. Other conventional manufacturing processes, such as machining, molding, extruding, and combinations thereof, may also be used as will be understood by one of ordinary skill in the art.

In some embodiments, the first end 104, which may be a superior end, includes a male coupling element 108, which may take the form of a threaded protrusion. The male coupling element 108 may be sized and configured to engage a female coupling element (e.g., a threaded hole) of another component of a multi-component prosthesis stem. While male coupling element 108 is shown as a threaded protrusion, one of ordinary skill in the art will understand that male coupling element 108 may be implemented in other ways, such as those disclosed in U.S. Provisional Patent Application No. 63/169,306, filed Apr. 1, 2021 and which is incorporated by reference in its entirety. Examples of such male coupling elements include, but are not limited to, a tapered protrusion or a protrusion including a detent, to identify only a couple of possibilities. It should also be appreciated that in some embodiments, such as when the stem component 100 is to be implemented as a top or superior component, the male coupling element may be omitted and the first end 104 may simply be tapered or conical.

As best seen in FIGS. 1 and 2, body 102 may include one or more anti-rotation features 110 that extend outwardly along a length of the body 102. The anti-rotation features 110 are sized and configured to resist rotation of the stem. In some embodiments, the anti-rotation features 110 may take the form of fins that extend outwardly from and along a length of (e.g., axially between the first end 104 and second end 106) the body 102. While eight anti-rotation features 110 are shown, it should be understood that fewer or more anti-rotation features may be provided. Further, while the anti-rotation features 110 are shown as being continuous fins that extend along the length of the body 102, the anti-rotation features 110 can take other forms, such as a plurality of interrupted fins and/or other type of projections that are arranged linearly and/or offset from one another. Further, while the anti-rotation features 110 are shown as being generally trapezoidal in shape, the anti-rotation features 110 can take other forms, such as teardrop, triangular, or other shape as will be understood by one of ordinary skill in the art.

Body 102 may further include one or more engagement elements 112 each sized and configured to be engaged by a tool. For example, the one or more engagement elements 112 may take the form of a hole, opening, or recess, which may have a geometry that is configured to be engaged by a tool for applying torque to the stem component 100. In the illustrated example, the one or more engagement elements 112 are in the form of diamond-shaped holes that extends through the body 102. In some embodiments, the one or more engagement elements 112 are disposed between anti-rotation features 110 such that adjacent anti-rotation features 110 are separated by an engagement element of the one or more engagement elements 112. The one or more engagement elements 112 are sized to receive a complementary-shaped torquing instrument that may be used to couple together multiple stem components and/or to apply additional torque during a removal process. Providing multiple engagement elements 112 around the periphery of body 102 advantageously enables for engagement by a tool regardless of the clocking of the thread or orientation during insertion.

In some embodiments, the one or engagement elements 112 may be disposed at intervals such that an engagement element is not disposed between each pair of adjacent anti-rotation features, such as shown in the examples illustrated in 12, 13, 17, 18, 22, 23, 27, and 28.

As best seen in FIG. 2, second end 106, which may be an inferior end, may include a female coupling element 114 for coupling the stem component 100 to another prosthesis component, such as another stem component and/or a tray, for example. In some embodiments, the female coupling element 114 may take the form of an internally threaded hole that is sized and configured to receive a male coupling element, such as a threaded protrusion. However, as shown in FIGS. 6-16 and 27-31 and discussed below, the female coupling element 114 may have other forms, such as a tapered hole 130 (shown in FIG. 6) that is sized and configured to engage a tapered male protrusion to form a Morse taper or other friction fit connection, such as provided by a tray or other stem component, as will be understood by one of ordinary skill in the art.

In some embodiments, stem 100 includes an engagement element 116 and an engagement element 126 that are located at or accessible via second end 106. For example, the engagement element 116 may include a depression or interface for engaging a torquing instrument, which may be a different type of torquing instrument from the torquing instrument for engaging the one or more engagement elements 112. As shown in FIG. 2, the engagement element 116 may be a gear-shaped depression extending inwardly from second end 106 and include a plurality of frustum-shaped depressions 118 radiating outwardly about (e.g., concentric with) the hole of female coupling element 114. The frustum-shaped depressions 118 are arranged such that their wider adjacent to the hole of the female coupling element 114 and narrower as they approach the perimeter of the body 102. While ten frustum-shaped depressions 118 are illustrated in FIG. 2, it should be understood that fewer or more frustum-shaped depressions 118 may be provided. Further, while the frustum-shaped depressions 118 are shown as extending into body 102 and having a planar inner or bottom surface 120 and side walls 122 that extend perpendicularly from bottom surface 120, the engagement element 116 may take other configurations or shapes.

Figure 3:
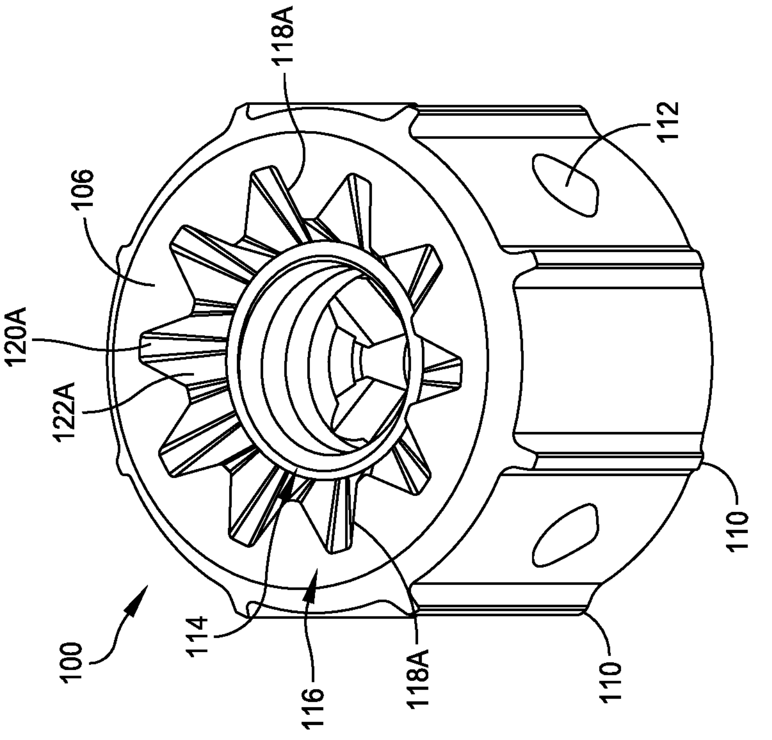
FIG. 3 is a bottom side isometric view of another example of a stem component, in accordance with some embodiments.

For example, FIG. 3 illustrates another example of an engagement element 116 including a plurality of frustum-shaped depressions 118A extending into second end 106 with an angled bottom surface 120A and side walls 122A. In some embodiments, bottom surface 120A tapers along a length of the frustum-shaped depression such that a surface closer to the female coupling element 114 is deeper (e.g., farther away from second end 106) than a surface closer to the outer periphery of body 102 (e.g., farther away from female coupling element 114). Side walls 122A may be oriented at angles other than right angles relative to the bottom surface 120A and/or a surface of second end 106.

The relative angles between the surfaces 120A, 122A, as well as the geometric shape and size, may be varied in order to adjust a maximum amount of torque that may be applied by a torquing instrument to component 100. For example, the interface between the engagement element 116 and a torquing instrument or tool may be designed to transfer a maximum amount of torque from the tool to the component 100 to avoid over-torquing of the prosthesis (e.g., the multiple components of a multi-component stem). In some embodiments, the interface is designed to cause the torquing instrument to disengage (e.g., cam) from engagement element 116 when a torque is applied that exceeds the maximum torque. In some embodiments, the interface is designed to prevent over-torquing by having the torquing instrument deform if too much torque is applied. One of ordinary skill in the art will understand that the maximum amount of torque for the interface may be predetermined based on a number of parameters, including coefficient of friction between the two materials (e.g., the material and/or surface finish of the torquing instrument and component 100 and/or surface hardness of the torquing instrument and component 100) and the geometry of the interface.

Figure 4:
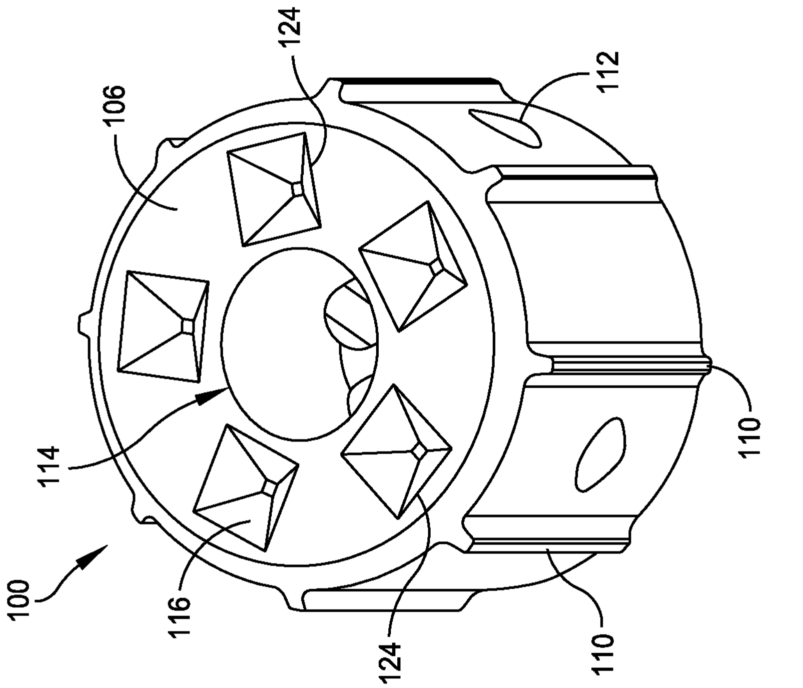
FIG. 4 is a bottom side isometric view of another example of a stem component, in accordance with some embodiments.

As noted above, engagement element 116 may take other forms other than the plurality of radially extending frustum-shaped depressions 118, 118A, such as those illustrated in FIGS. 2, 3, 6, 15, 16, 20, 21, 25, and 26. For example, engagement element 116 may be implemented for receiving a star driver, a hex driver, a square driver, or any other tool for applying torque as will be understood by one of ordinary skill in the art. In the example illustrated in FIG. 4, the engagement element 116 takes the form of a plurality of square pyramids 124 that extend inwardly into second end 106 and are arranged around female coupling element 114. Here again, while five square pyramids 124 are shown, the engagement element 116 may implemented as fewer or more square pyramids 124 or be implemented in other shapes and sizes. Further, while the engagement element 116 is shown as including a plurality of individual elements equidistantly spaced around female coupling element 114, they may be unequally spaced and/or placed at different distances from female coupling element 114.

Incorporating the engagement element 116 into the second side/end 106 advantageously increases the surface area along the body 102 between ends/sides 104, 106 that may be utilized for bone ingrowth. For example, the body 102 may be formed from a porous material and/or include areas of porous material that promote bone ingrowth. Examples of such materials include, but are not limited to, ADAPTIS™ 3D printed, porous metal, available from Wright Medical Technology, Inc., Tritanium® porous metal, available from Stryker, and/or porous ceramics, to list only a few possibilities. Further, the incorporation of engagement element 116 into the second end/side 106 enables the overall length or height of a stem component to be reduced, which allows the overall length of the stem prosthesis to be adjusted.

Referring again to FIG. 2, in some embodiments, the engagement element 126 may be disposed in communication with the female coupling element 114 and take the form of a hole that includes a plurality of inwardly extending ridges 128. For example and as best seen in FIGS. 5, 6, 11, 16, 21, and 26, the ridges 128 are oriented such that they are concentric with the hole and are angled upward toward the first end 104. The angling of the ridges 128 facilitates the insertion of a removal tool and then resisting disengagement of the removal tool from the stem component 100. For example, when a removal tool is inserted into the third engagement element 126, the ridges 128 may be deformed by or bite into the removal tool to facilitate coupling between the removal tool and the stem component 100. In some embodiments, a central axis defined by the hole of the female coupling element 114 is collinear with a central axis defined by the engagement element 126. In some embodiments a central axis defined by the hole is aligned with a central axis defined by the body 102.

Figure 6:
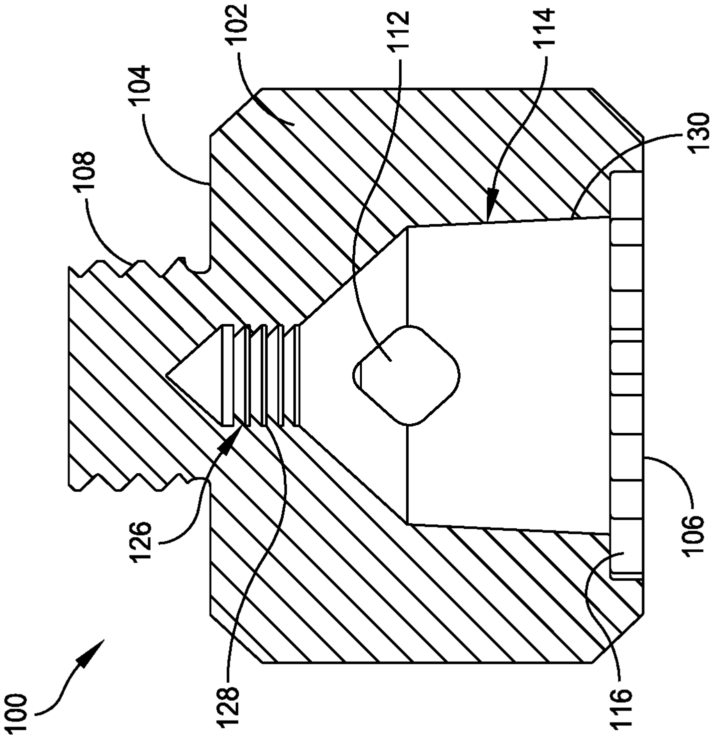
FIG. 6 is one example of a sectional view of another example of a stem component, in accordance with some embodiments.
Figure 5:
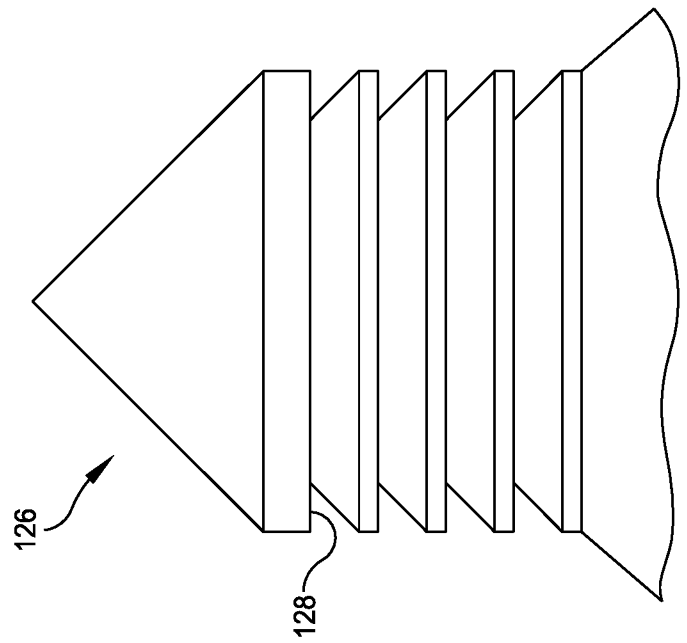
FIG. 5 is a detailed view of one example of an engagement feature for a stem component, in accordance with some embodiments.
Figure 7:
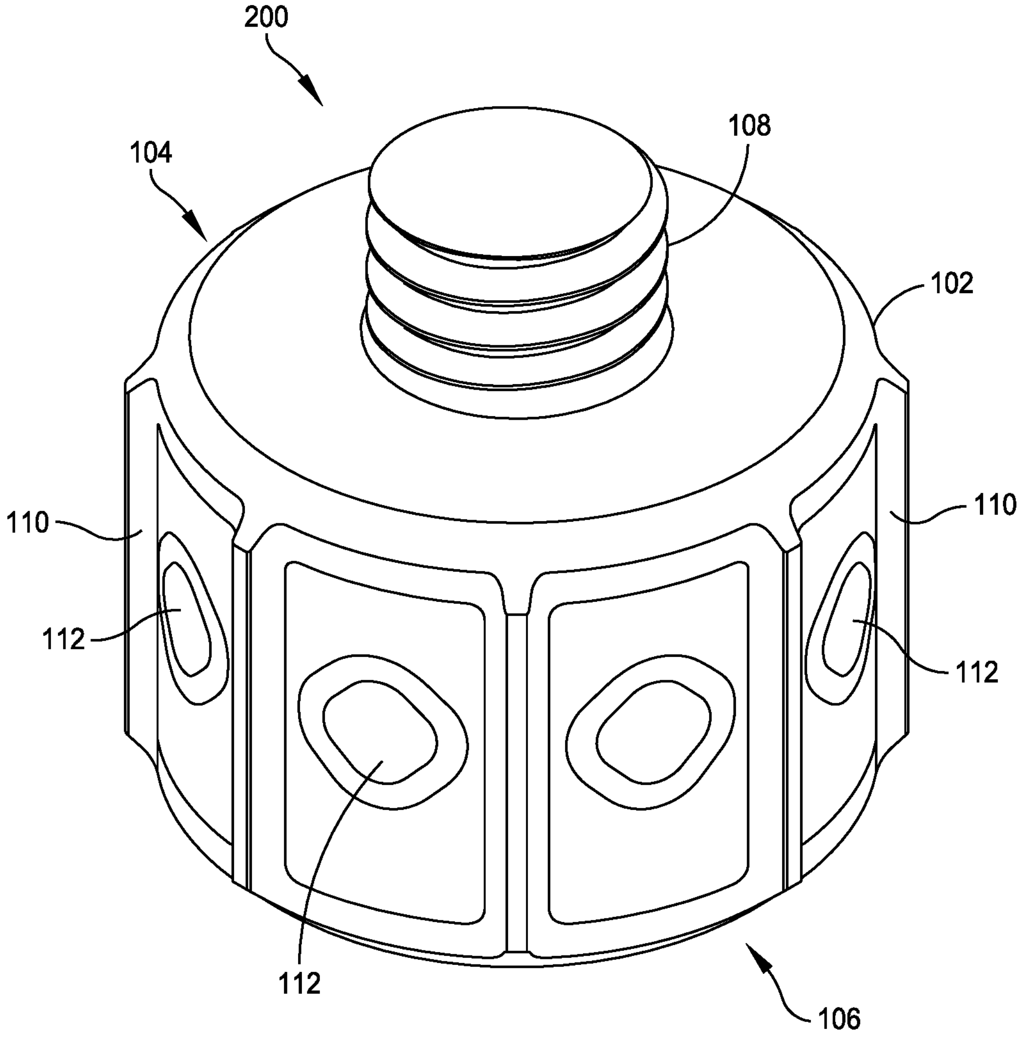
FIG. 7 is a front side isometric view of another example of a stem component, in accordance with some embodiments.
Figure 8:
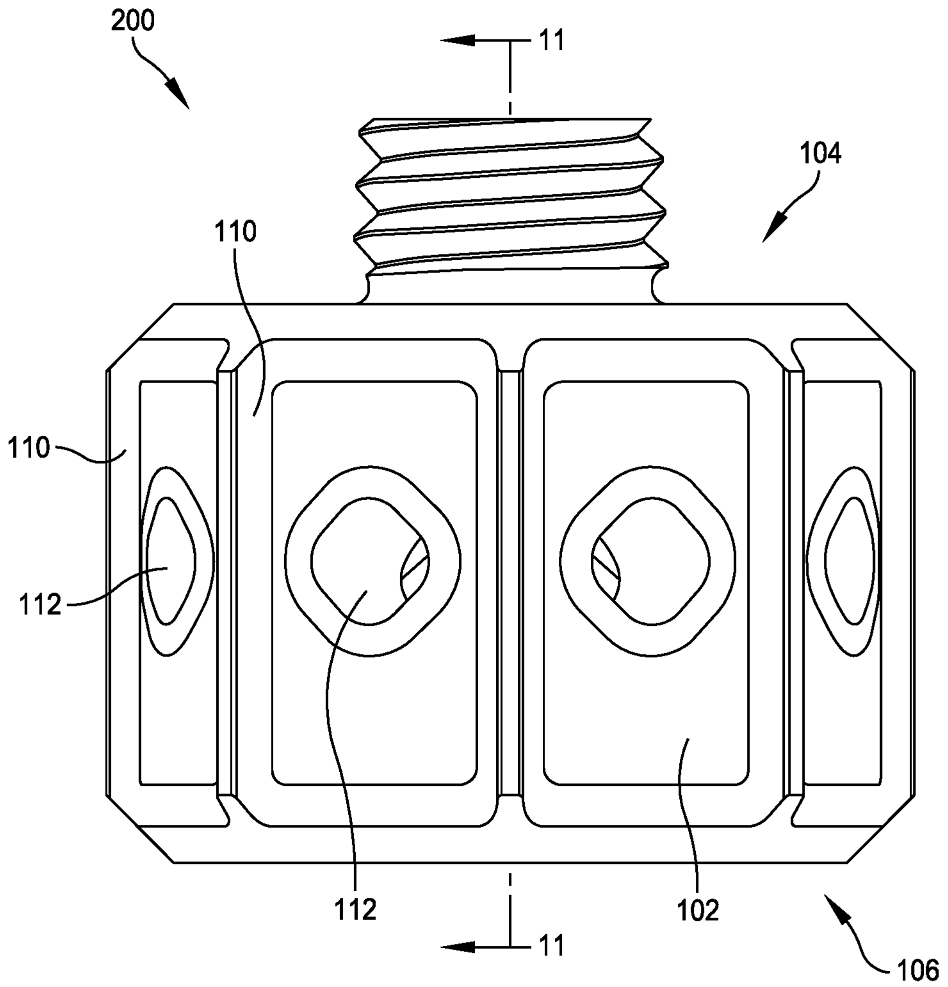
FIG. 8 is a side view of the stem component illustrated in FIG. 7, in accordance with some embodiments.
Figure 9:
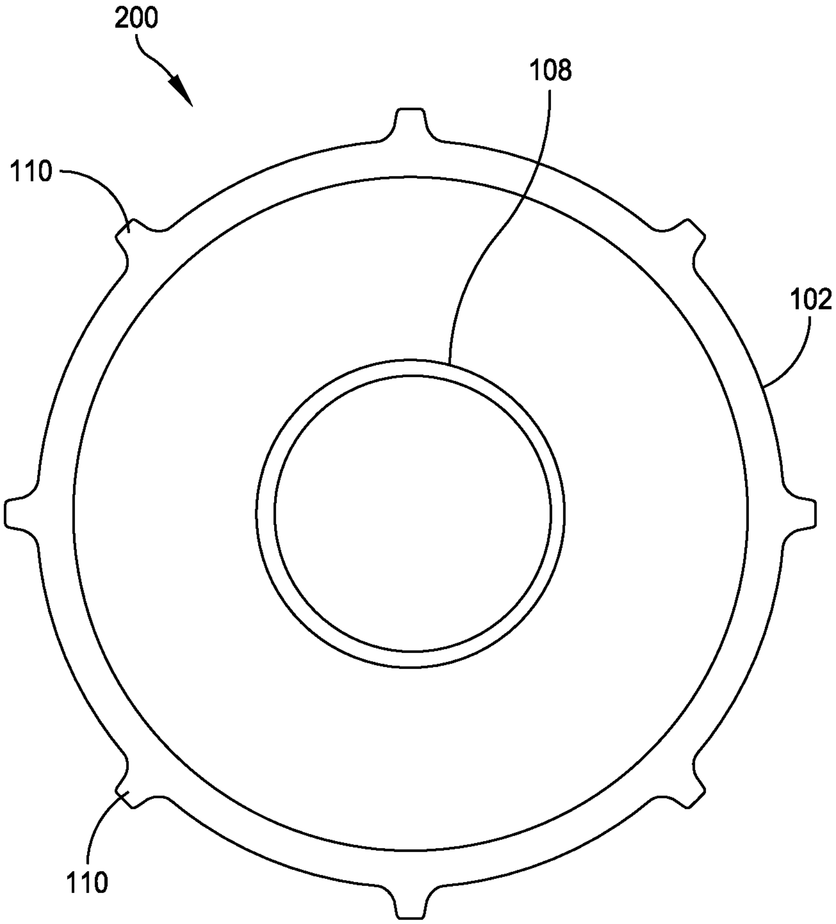
FIG. 9 is a top side view of the stem component illustrated in FIG. 7, in accordance with some embodiments.
Figure 11:
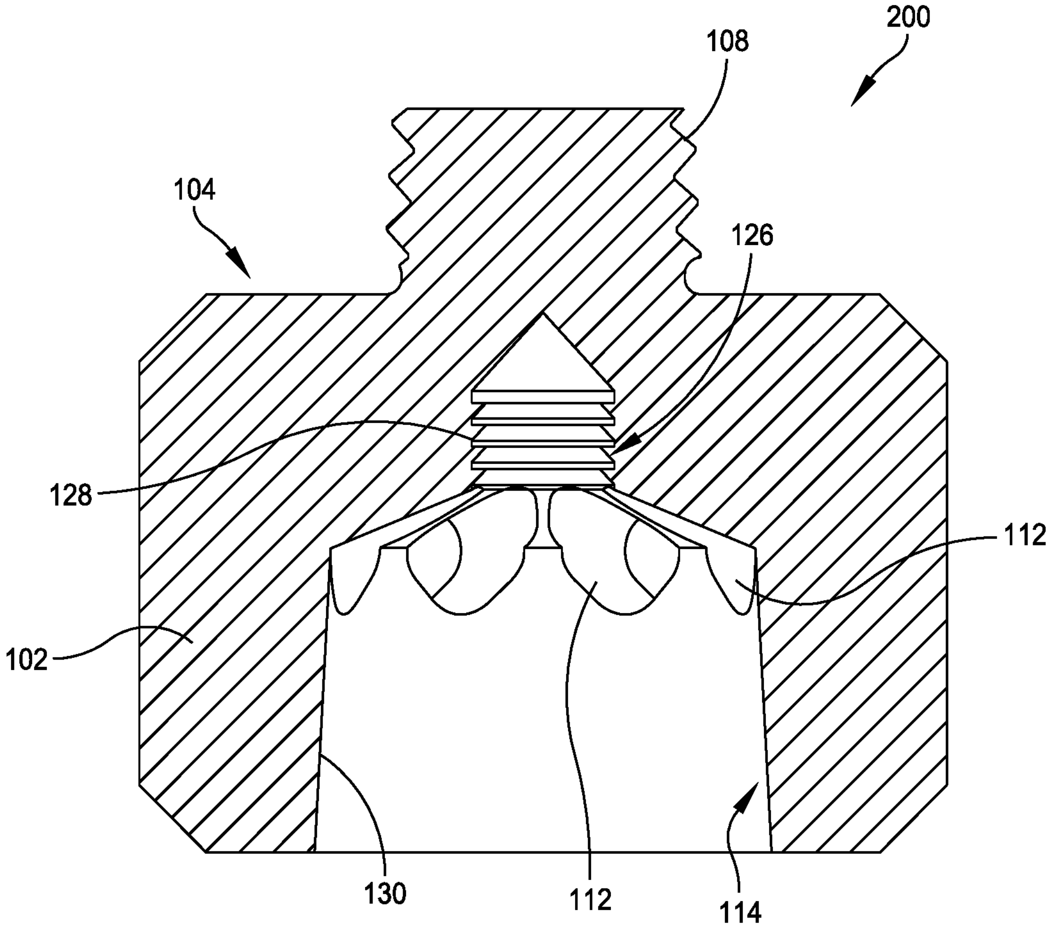
FIG. 11 is a cross-sectional view of the stem component illustrated in FIG. 7 taking along line 11-11 in FIG. 8, in accordance with some embodiments.
Figure 16:
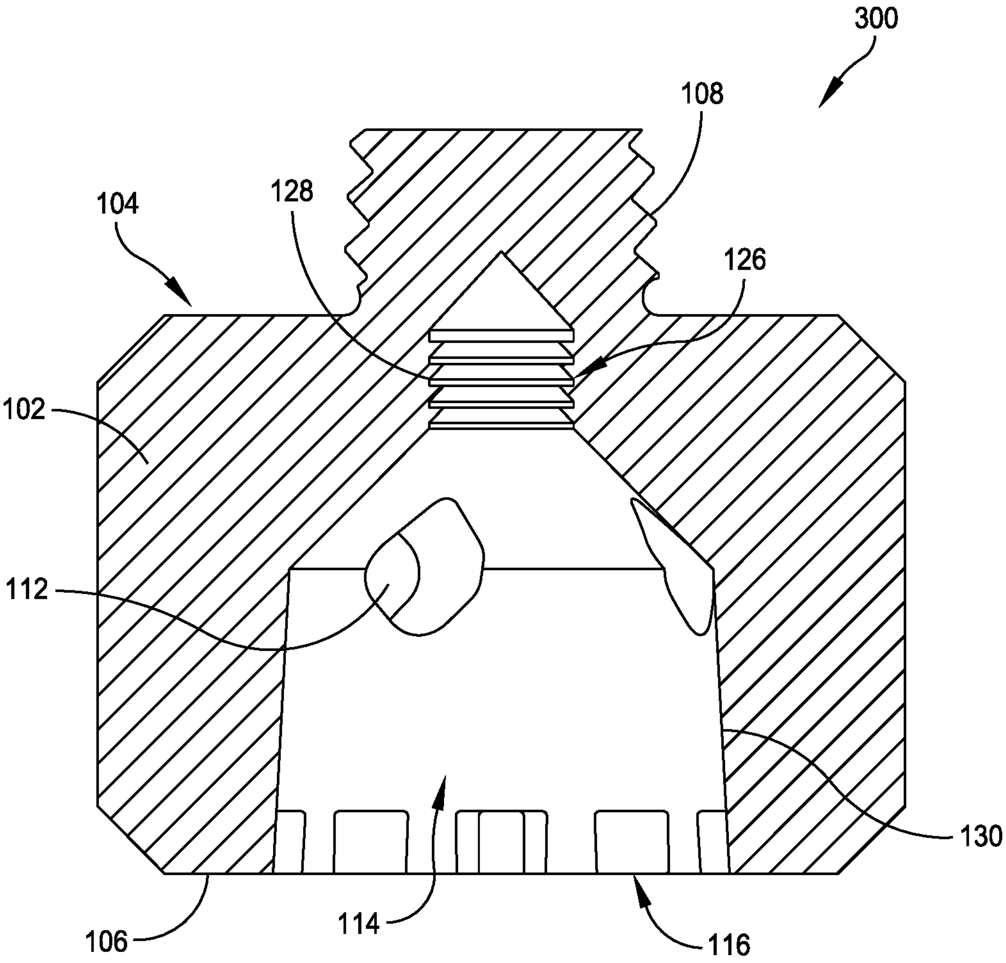
FIG. 16 is a cross-sectional view of the stem component illustrated in FIG. 12 taken along line 16-16 in FIG. 13, in accordance with some embodiments.
Figure 31:
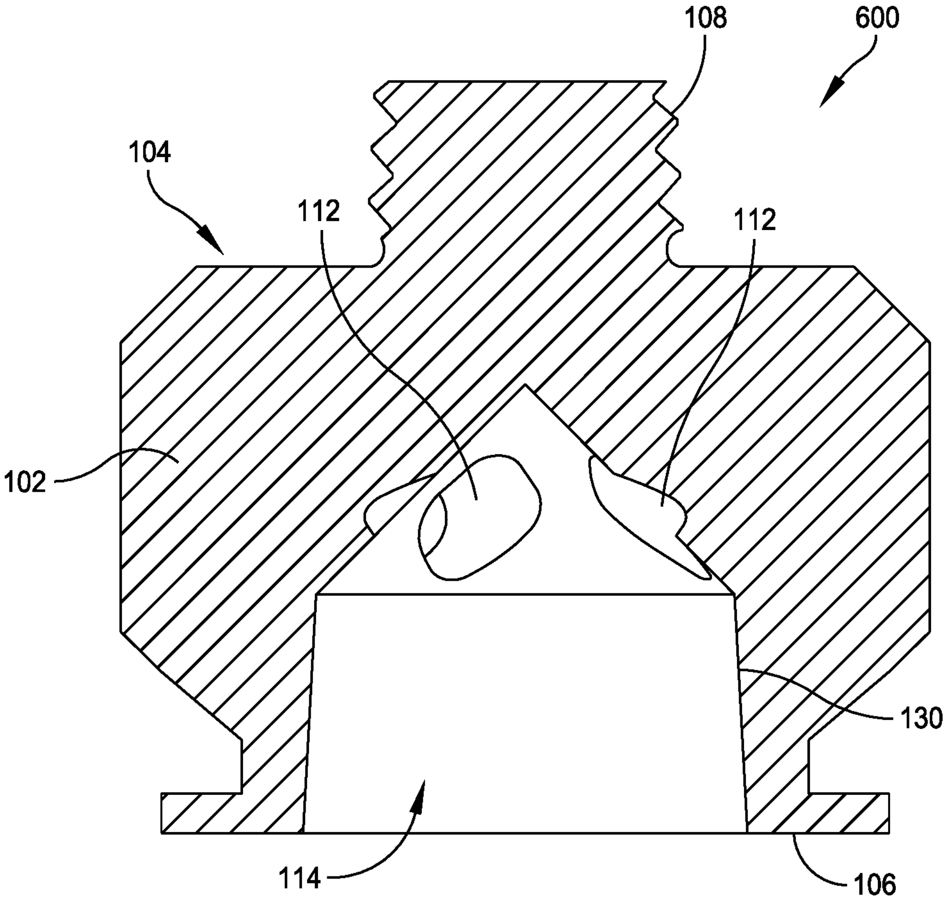
FIG. 31 is a cross-sectional view of the stem component illustrated in FIG. 27 taken along line 31-31 in FIG. 28, in accordance with some embodiments.

As noted above, FIG. 6 is a cross-sectional view of one example of a stem component 100 in which female coupling element 114 includes a tapered hole 130. FIGS. 11, 16, and 31 also illustrate examples of stem components 200, 300, 600 having a female coupling element 114 in the form of a tapered hole 130. Hole 130 may be designed to engage a protrusion to form a Morse taper connection, such as a protrusion that extends from a superior surface of a tray or from a superior surface of another prosthesis component, as will be understood by one of ordinary skill in the art. As shown in FIG. 6, the engagement element 126 may be formed in communication with tapered hole 130 such that engagement element 126 is disposed at least partially between a superior-most portion of female coupling element 114 and first surface 104 and/or male coupling element 108. In such embodiments, engagement element 126 is accessible via female coupling element 114.

FIGS. 7-11 illustrate another example of a stem component, in accordance with some embodiments. Stem component 200 may include a body 102 having a male coupling element 108 located at a first end 104 and a female engagement element 114 located at a second end 106. Body 102 may include a plurality of anti-rotation features 110 extending along its length (e.g., between the first end 104 and second end 106). One or more engagement elements 112 may be disposed along a length of the body 102 with a respective engagement element 112 being disposed between adjacent anti-rotation features 110.

Figure 10:
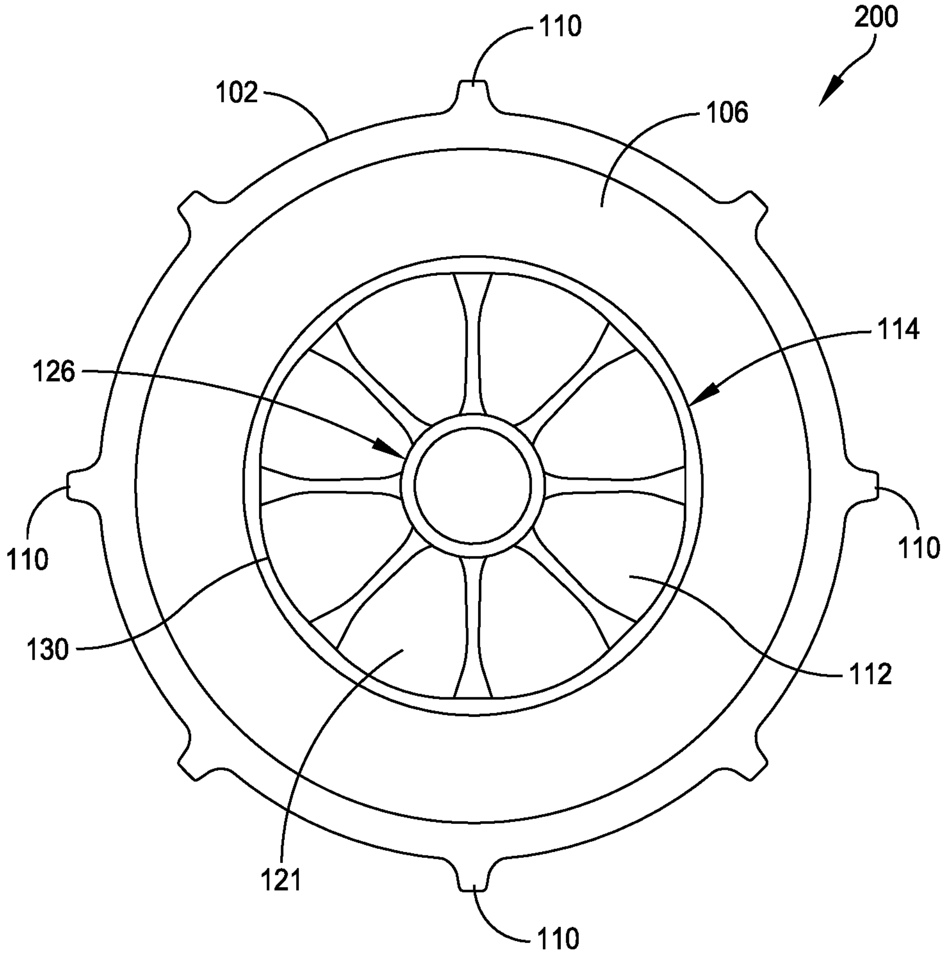
FIG. 10 is a bottom side view of the stem component illustrated in FIG. 7, in accordance with some embodiments.

As best seen in FIGS. 10 and 11, the female engagement element 114 may take the form of a tapered hole 130 that extends inwardly from end 106. An engagement element 126 may be disposed in communication with the tapered hole 130 such that engagement element 126 is accessible via tapered hole 130. In some embodiments, the engagement element 126 may include a plurality of concentric ridges 128 as described above. The stem component 200 may differ from the stem component illustrated in FIGS. 1 and 2 in that it the engagement element 116 is omitted. In such embodiments, the anti-rotation elements 110 and/or engagement elements 112 may be used to apply to torque to the stem component 200.

Figure 12:
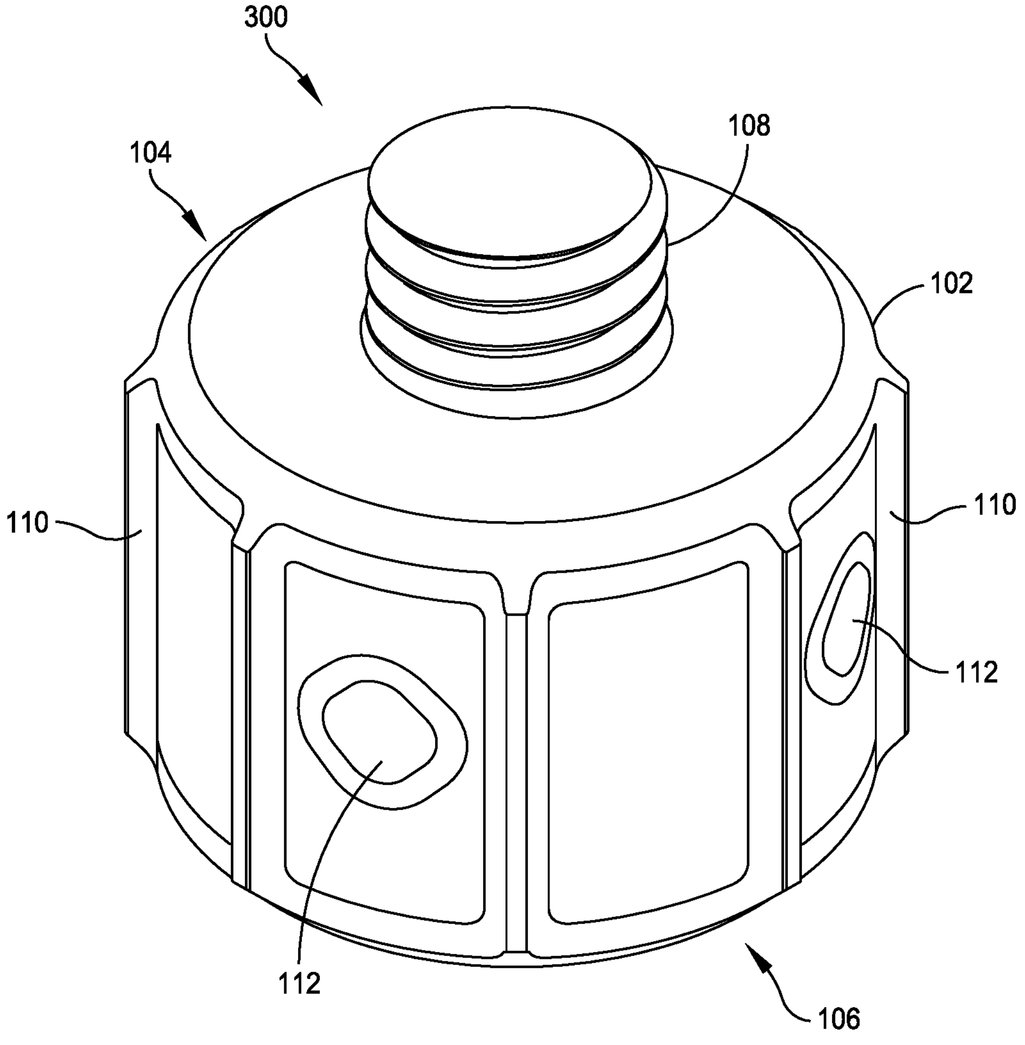
FIG. 12 is a front side isometric view of another example of a stem component, in accordance with some embodiments.
Figure 13:
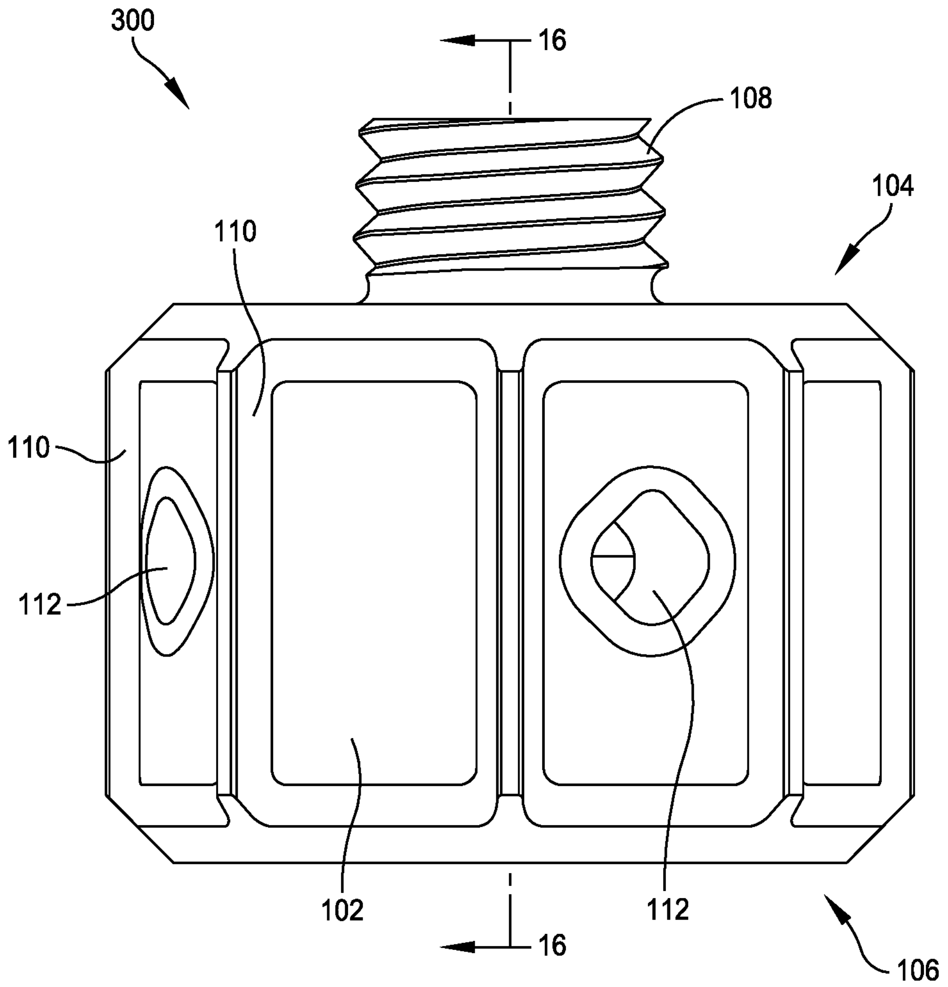
FIG. 13 is a side view of the stem component illustrated in FIG. 12, in accordance with some embodiments.
Figure 14:
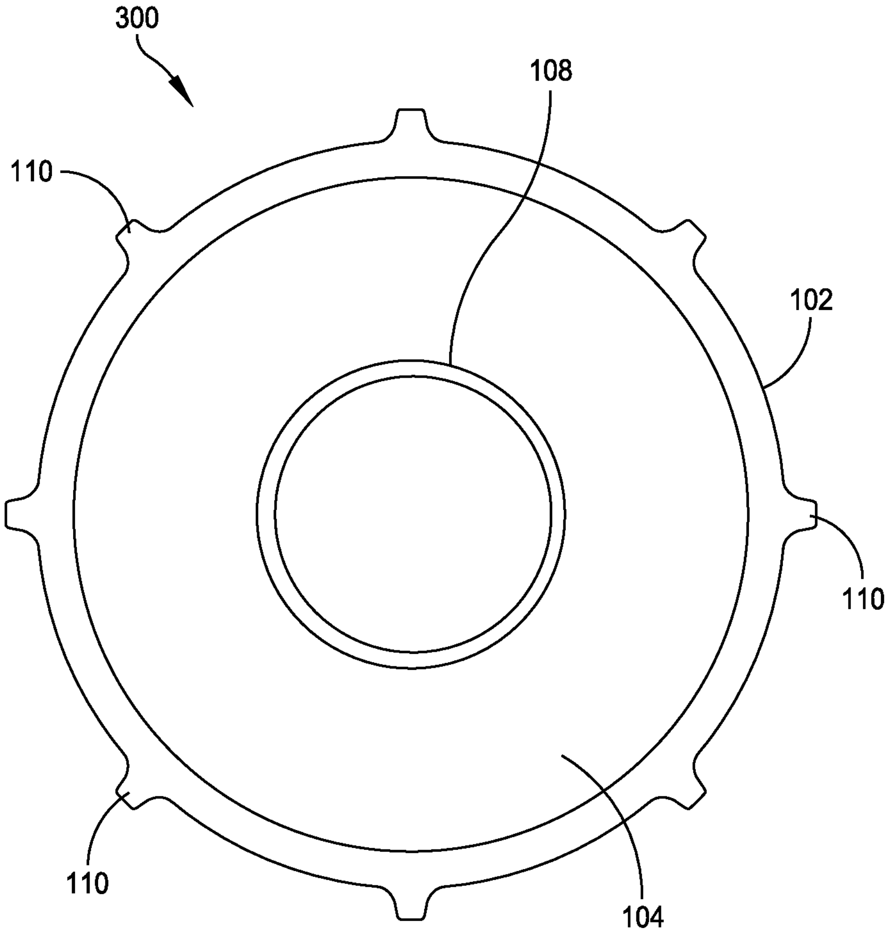
FIG. 14 is a top side view of the stem component illustrated in FIG. 12, in accordance with some embodiments.

FIGS. 12-16 illustrate another example of a stem component in accordance with some embodiments. Stem component 300 may include a body 102 having a male coupling element 108 located at a first end 104 and a female engagement element 114 located at a second end 106. Body 102 may include a plurality of anti-rotation features 110 extending along its length (e.g., between the first end 104 and second end 106). One or more engagement elements 112 may be disposed along a length of the body 102 with a respective engagement element 112 being disposed between adjacent anti-rotation features 110. As best seen in FIGS. 12 and 13, the engagement elements 112 may be arranged such that pairs of adjacent anti-rotation features 110 may alternatively have an engagement disposed therebetween, as opposed to each pair of adjacent anti-rotation features 110 having an engagement element 112 disposed therebetween, as shown in FIG. 1, for example.

Figure 15:
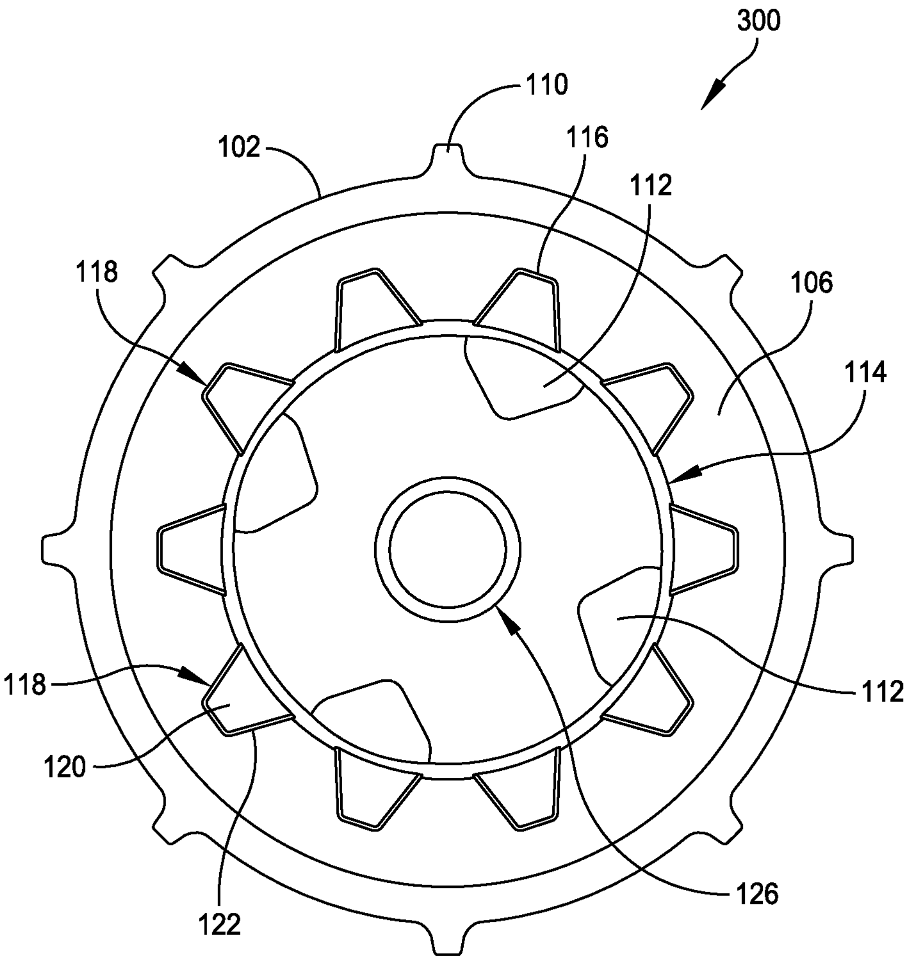
FIG. 15 is a bottom side view of the stem component illustrated in FIG. 12, in accordance with some embodiments.

As best seen in FIGS. 15 and 16, the female engagement element 114 may take the form of a tapered hole 130 that extends inwardly from end 106. An engagement element 126 may be disposed in communication with the tapered hole 130 such that engagement element 126 is accessible via tapered hole 130. In some embodiments, the engagement element 126 may include a plurality of concentric ridges 128 as described above.

Stem component 300 may include an engagement element 116 extending inwardly from end 106. Engagement element 116 may include a plurality of frustum-shaped depressions 118 that are radially arranged around the hole of the female engagement element 114, as best seen in FIGS. 15 and 16.

Figure 17:
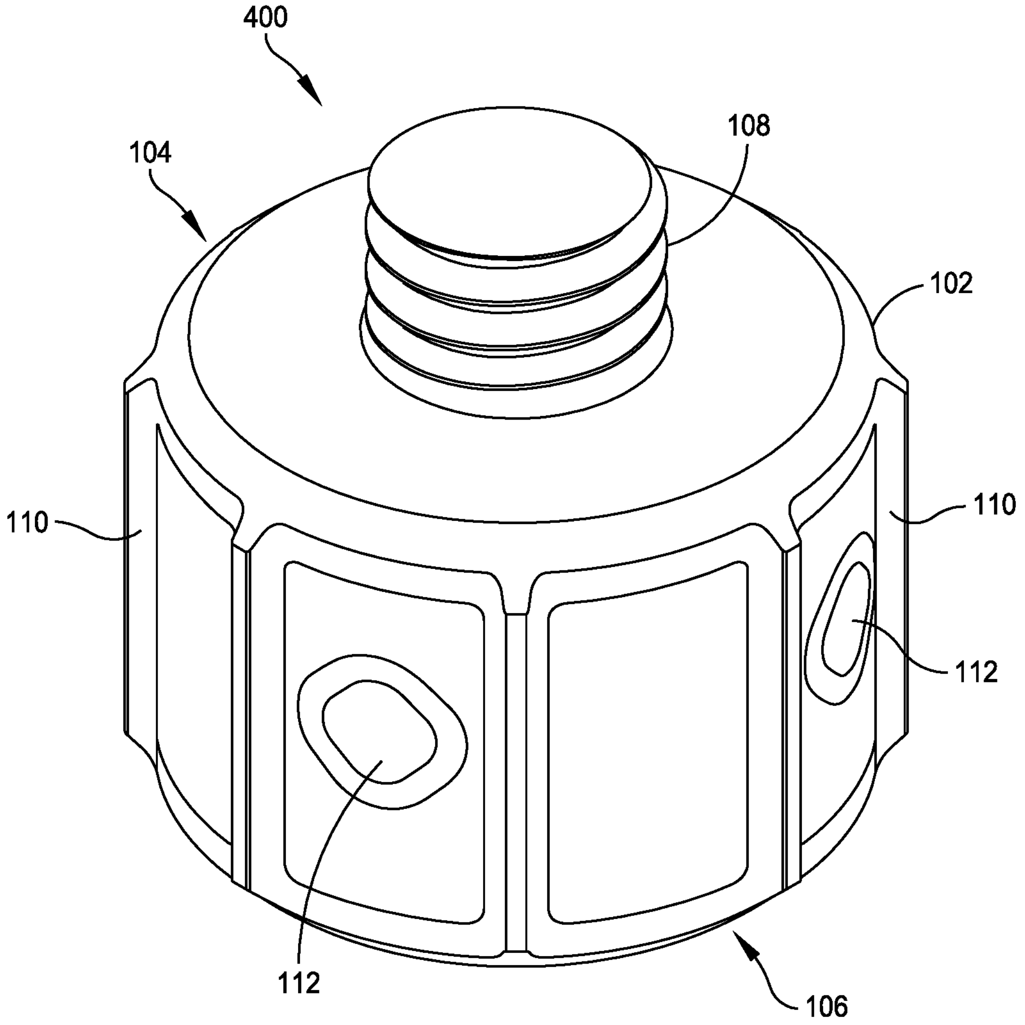
FIG. 17 is a front side isometric view of another example of a stem component, in accordance with some embodiments.
Figure 18:
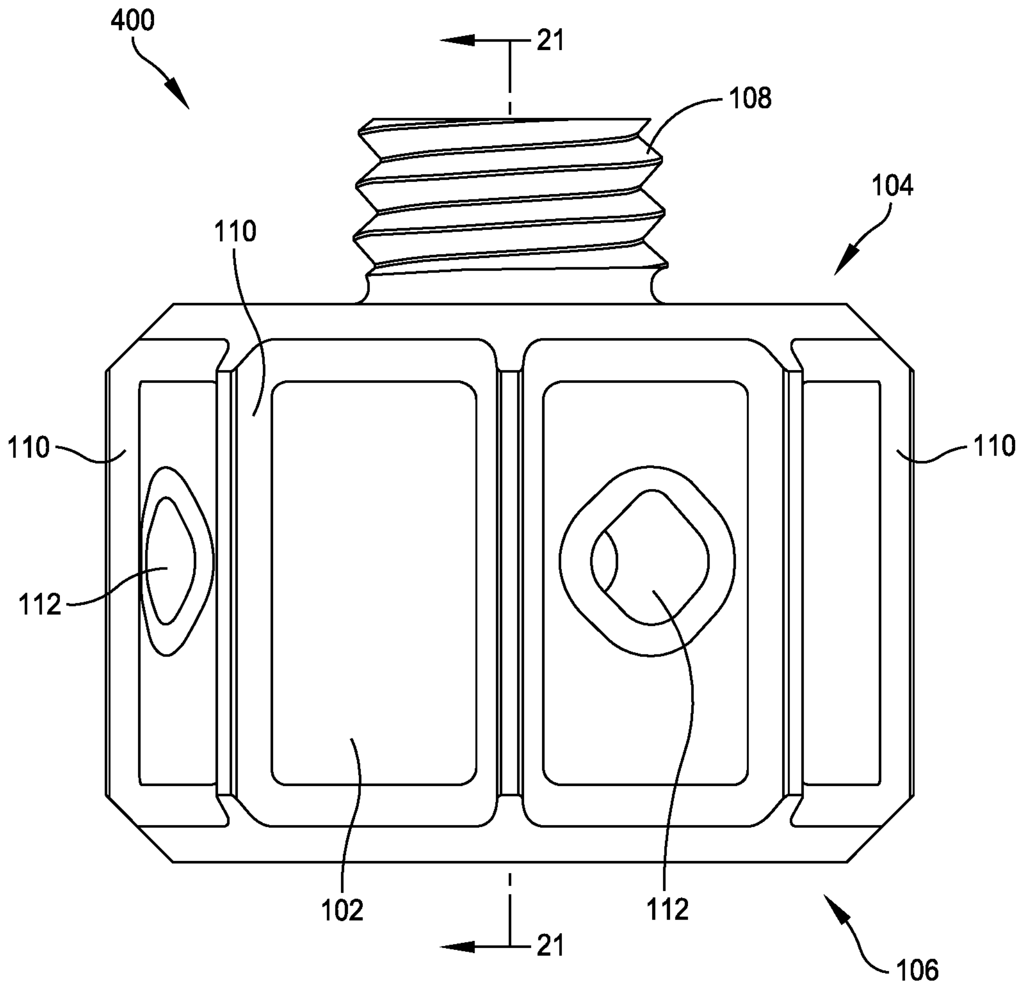
FIG. 18 is a side view of the stem component illustrated in FIG. 17, in accordance with some embodiments.
Figure 19:
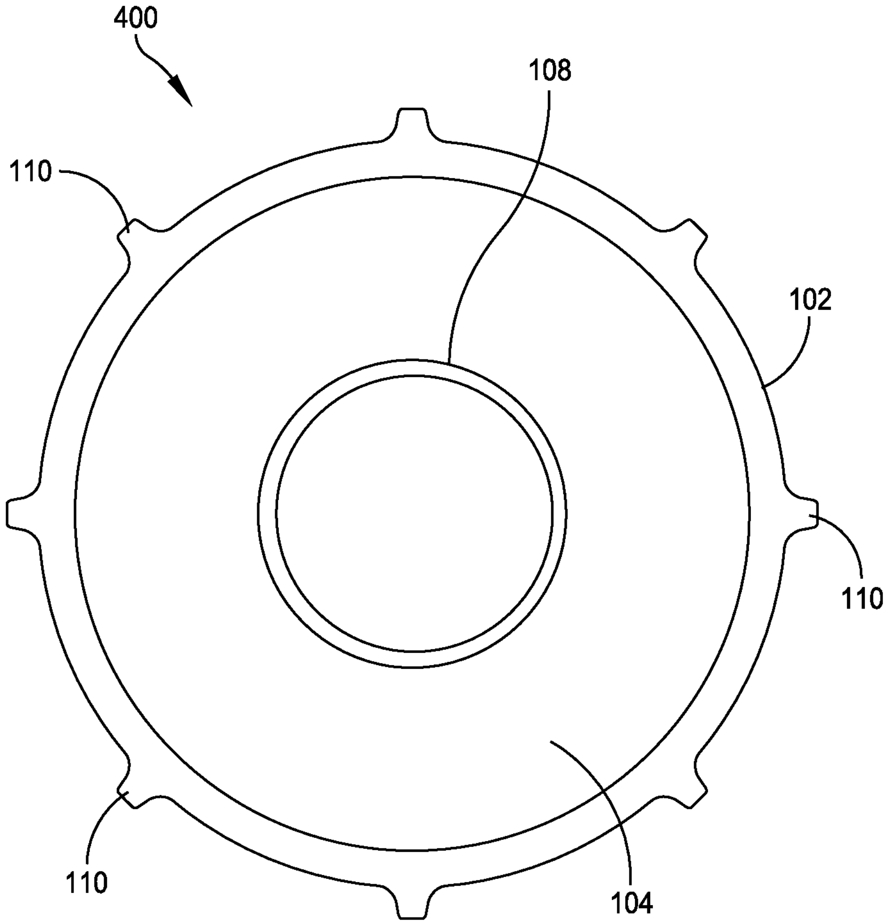
FIG. 19 is a top side view of the stem component illustrated in FIG. 17, in accordance with some embodiments.

FIGS. 17-21 illustrate another example of a stem component in accordance with some embodiments. Stem component 400 may include a body 102 having a male coupling element 108 located at a first end 104 and a female engagement element 114 located at a second end 106. Body 102 may include a plurality of anti-rotation features 110 extending along its length (e.g., between the first end 104 and second end 106). One or more engagement elements 112 may be disposed along a length of the body 102 with a respective engagement element 112 being disposed between adjacent anti-rotation features 110. As best seen in FIGS. 17 and 18, the engagement elements 112 may be arranged such that pairs of adjacent anti-rotation features 110 may alternatively have an engagement disposed therebetween, as opposed to each pair of adjacent anti-rotation features 110 having an engagement element 112 disposed therebetween, as shown in FIG. 1, for example.

Figure 21:
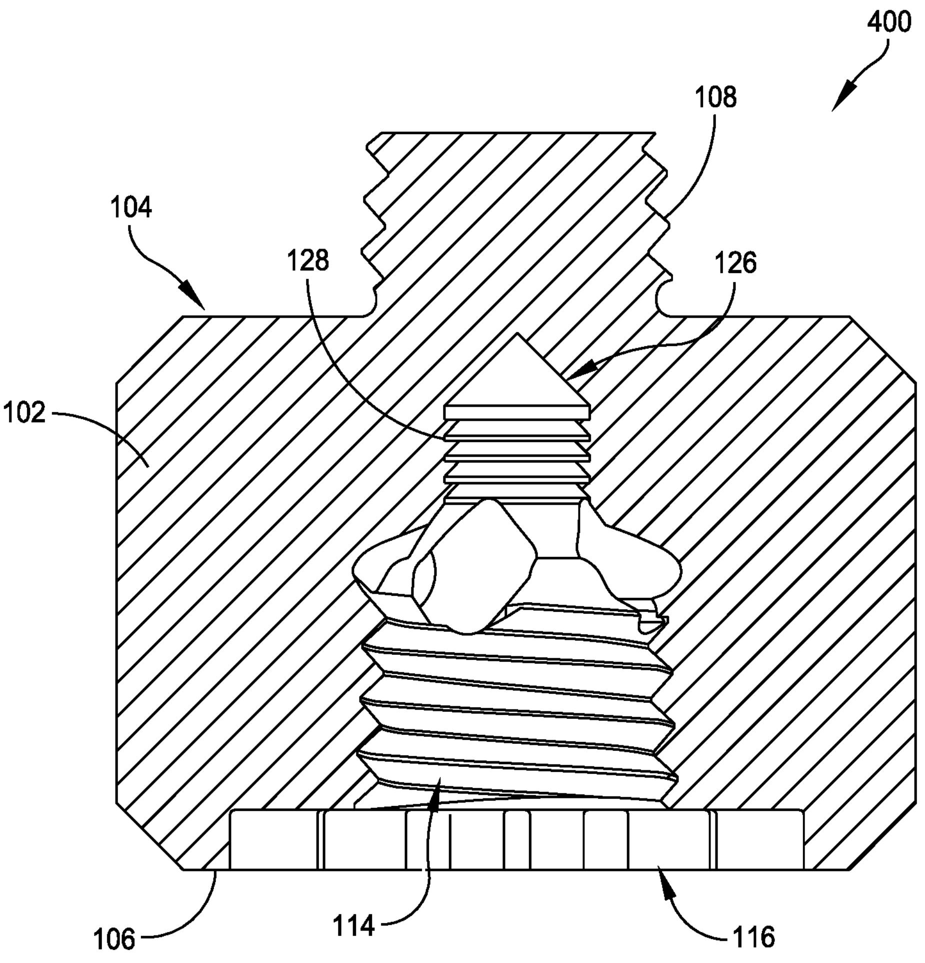
FIG. 21 is a cross-sectional view of the stem component illustrated in FIG. 17 taken along line 21-21 in FIG. 18, in accordance with some embodiments.

As best seen in FIG. 21, the female engagement element 114 may take the form of a threaded hole that extends inwardly from end 106. An engagement element 126 may be disposed in communication with the threaded hole of the female engagement element 114 such that engagement element 126 is accessible via the threaded hole of the female engagement element 114. In some embodiments, the engagement element 126 may include a plurality of concentric ridges 128 as described above.

Figure 20:
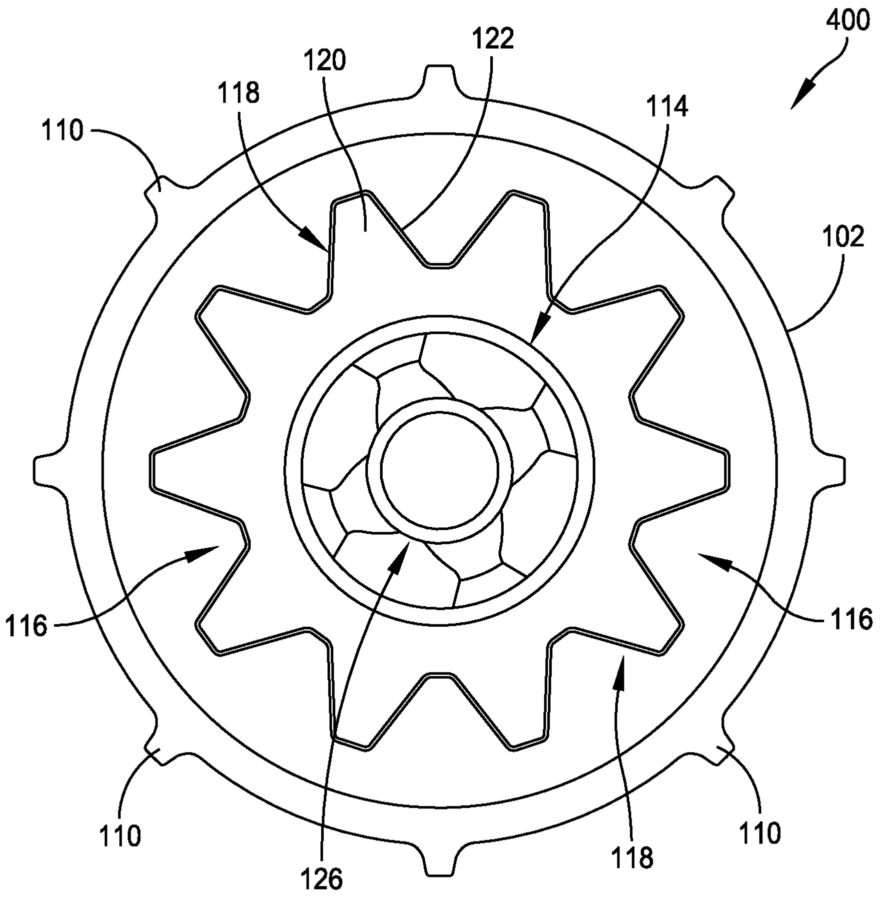
FIG. 20 is a bottom side view of the stem component illustrated in FIG. 17, in accordance with some embodiments.

Stem component 400 may include an engagement element 116 extending inwardly from end 106. Engagement element 116 may include a plurality of frustum-shaped depressions 118 that are radially arranged around the hole of the female engagement element 114, as best seen in FIGS. 20 and 21.

Figure 22:
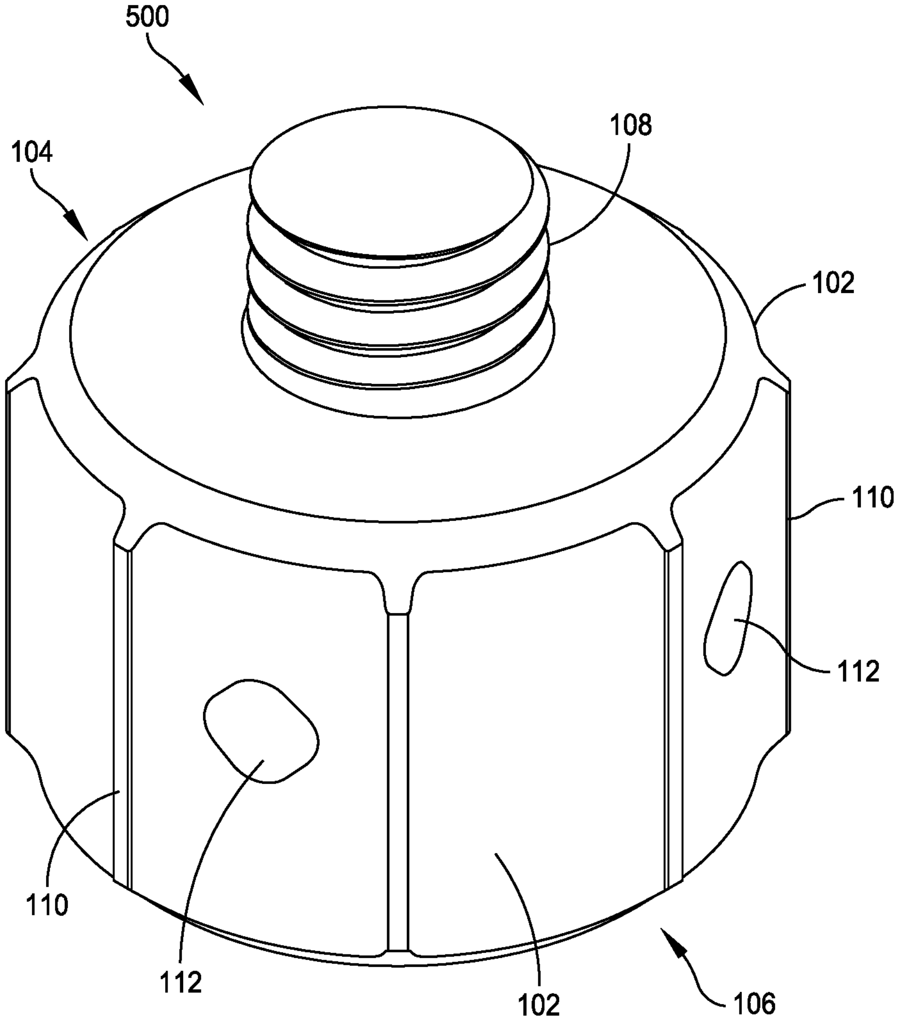
FIG. 22 is a front side isometric view of another example of a stem component, in accordance with some embodiments.
Figure 23:
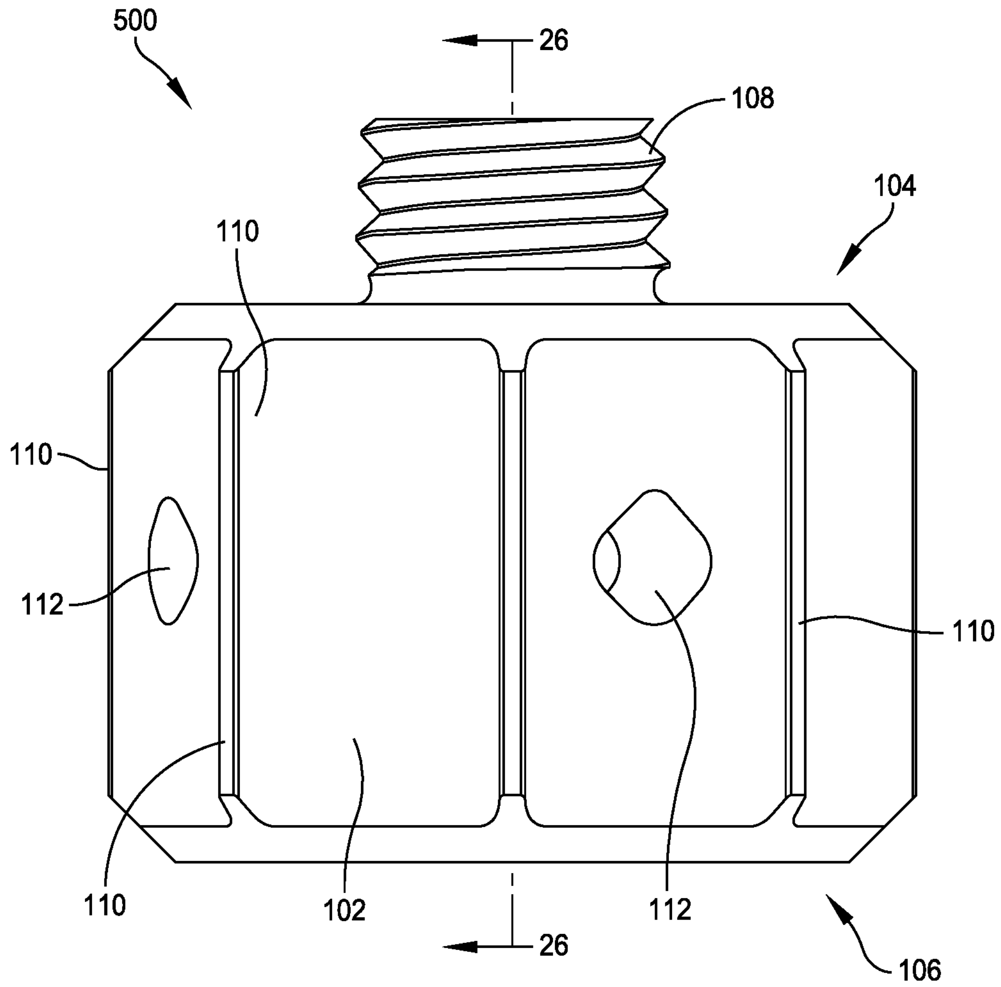
FIG. 23 is a side view of the stem component illustrated in FIG. 22, in accordance with some embodiments.
Figure 24:
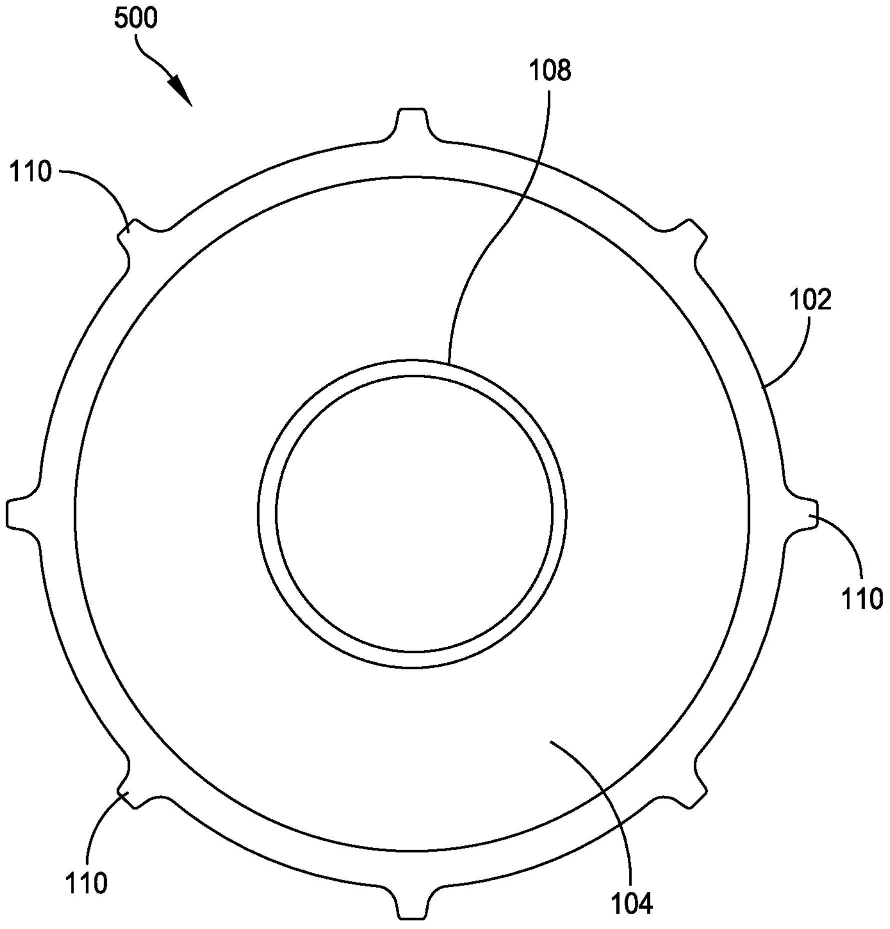
FIG. 24 is a top side view of the stem component illustrated in FIG. 22, in accordance with some embodiments.

FIGS. 22-26 illustrate another example of a stem component, in accordance with some embodiments. Stem component 500 may include a body 102 having a male coupling element 108 located at a first end 104 and a female engagement element 114 located at a second end 106. Male coupling element 108 may take the form of a threaded protrusion, as shown in FIGS. 22 and 23. Body 102 may include a plurality of anti-rotation features 110 extending along its length (e.g., between the first end 104 and second end 106). One or more engagement elements 112 may be disposed along a length of the body 102 with a respective engagement element 112 being disposed between adjacent anti-rotation features 110. As best seen in FIGS. 22 and 23, the engagement elements 112 may be arranged such that pairs of adjacent anti-rotation features 110 may alternatively have an engagement disposed therebetween, as opposed to each pair of adjacent anti-rotation features 110 having an engagement element 112 disposed therebetween, as shown in FIG. 1, for example.

Figure 26:
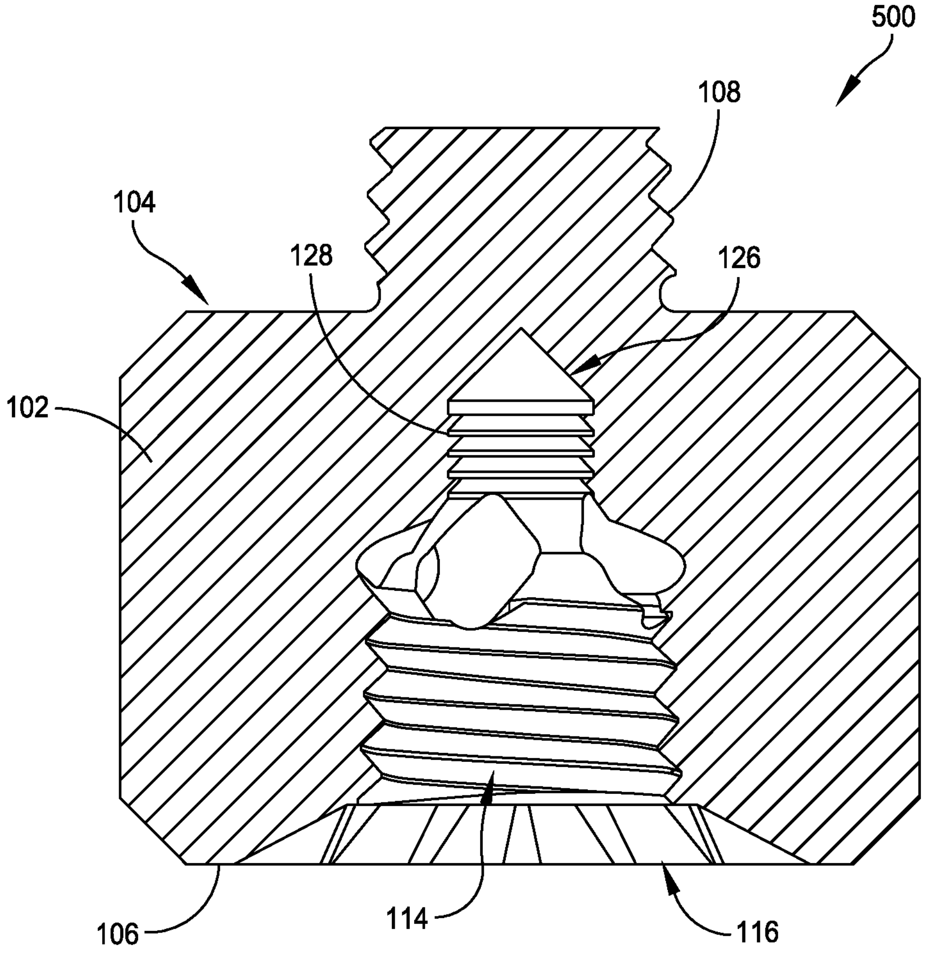
FIG. 26 is a cross-sectional view of the stem component illustrated in FIG. 22 taken along line 26-26 in FIG. 23, in accordance with some embodiments.

As best seen in FIG. 26, the female engagement element 114 may take the form of threaded hole that extends inwardly from end 106. An engagement element 126 may be disposed in communication with the threaded hole such that engagement element 126 is accessible via threaded hole. In some embodiments, the engagement element 126 may include a plurality of concentric ridges 128 as described above.

Figure 25:
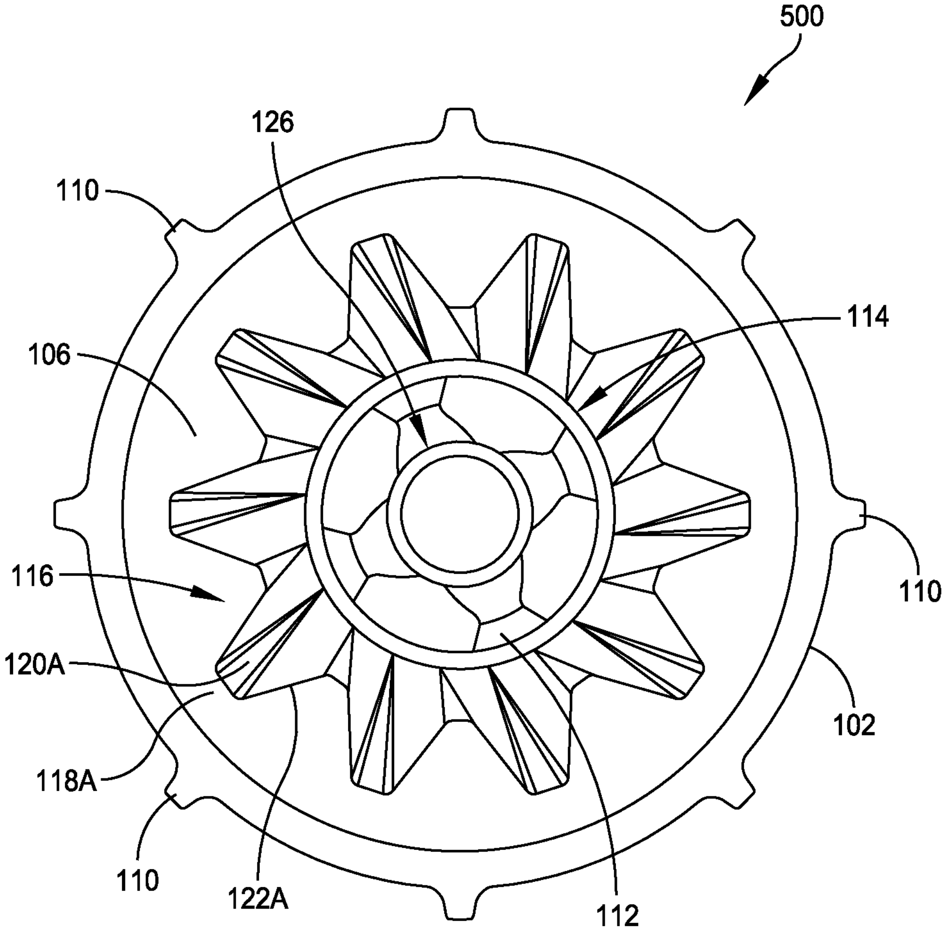
FIG. 25 is a bottom side view of the stem component illustrated in FIG. 22, in accordance with some embodiments.

Stem component 500 may include an engagement element 116 extending inwardly from end 106. Engagement element 116 may include a plurality of frustum-shaped depressions 118A that are radially arranged around the hole of the female engagement element 114, as best seen in FIGS. 25 and 26. As described above, the frustum-shaped depressions 118A may extend into surface 106 with angled bottom surfaces 120A and side walls 122A.

Figure 27:
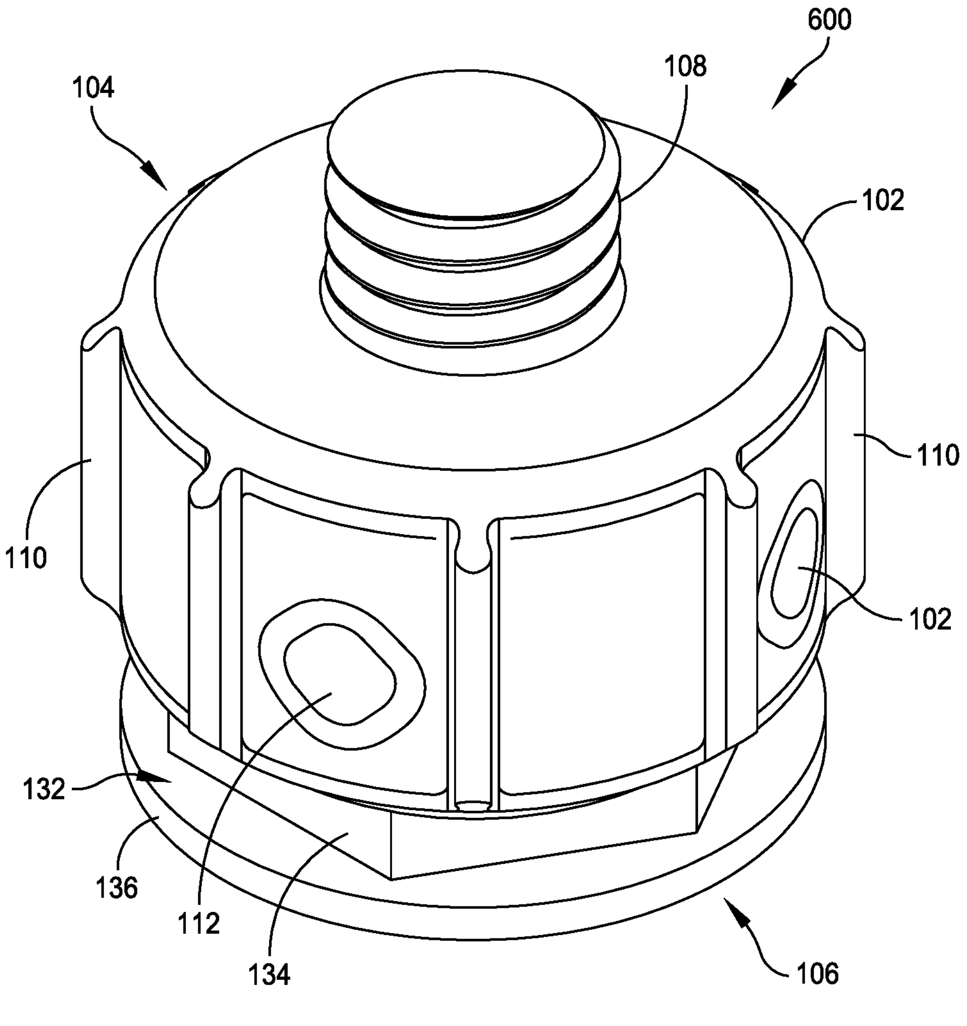
FIG. 27 is a front side isometric view of another example of a stem component, in accordance with some embodiments.
Figure 28:
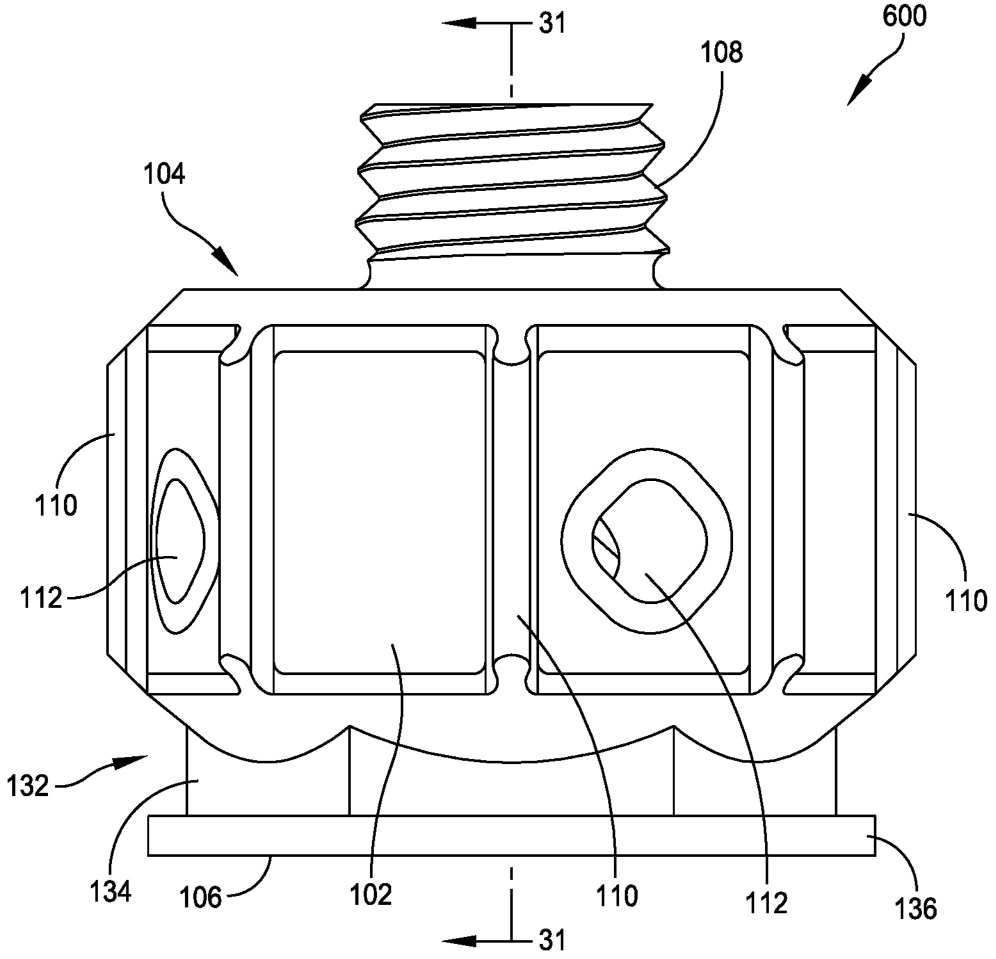
FIG. 28 is a side view of the stem component illustrated in FIG. 27, in accordance with some embodiments.
Figure 29:
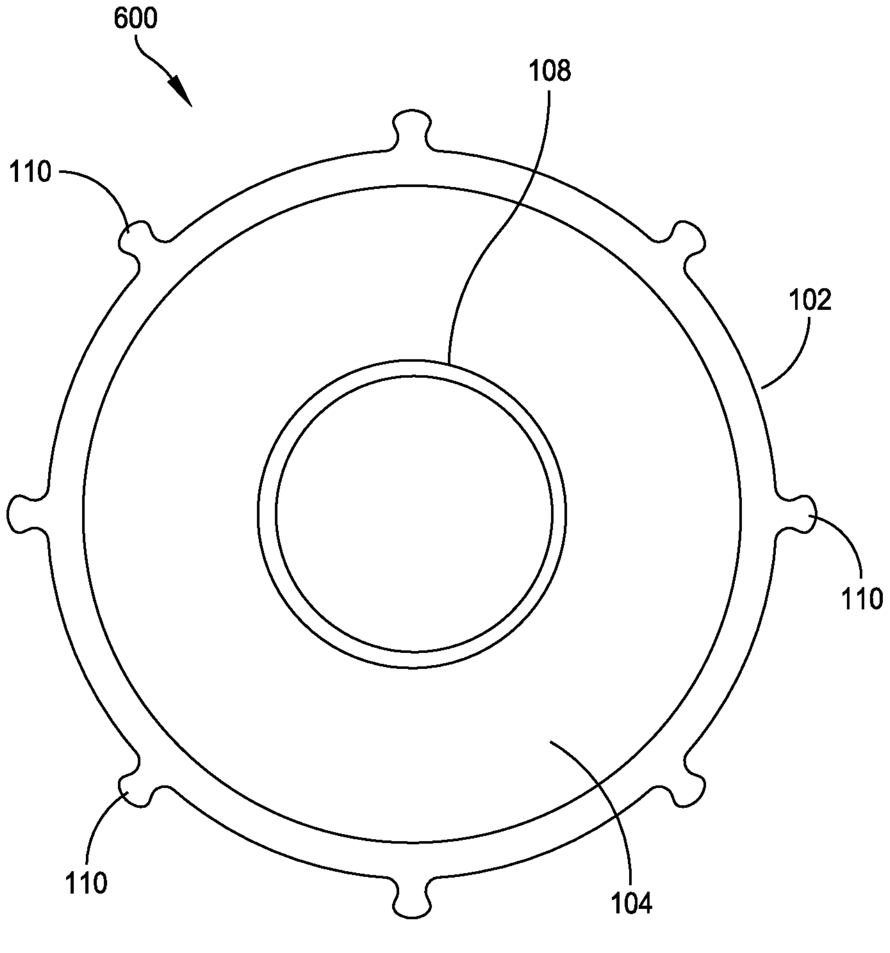
FIG. 29 is a top side view of the stem component illustrated in FIG. 27, in accordance with some embodiments.
Figure 30:
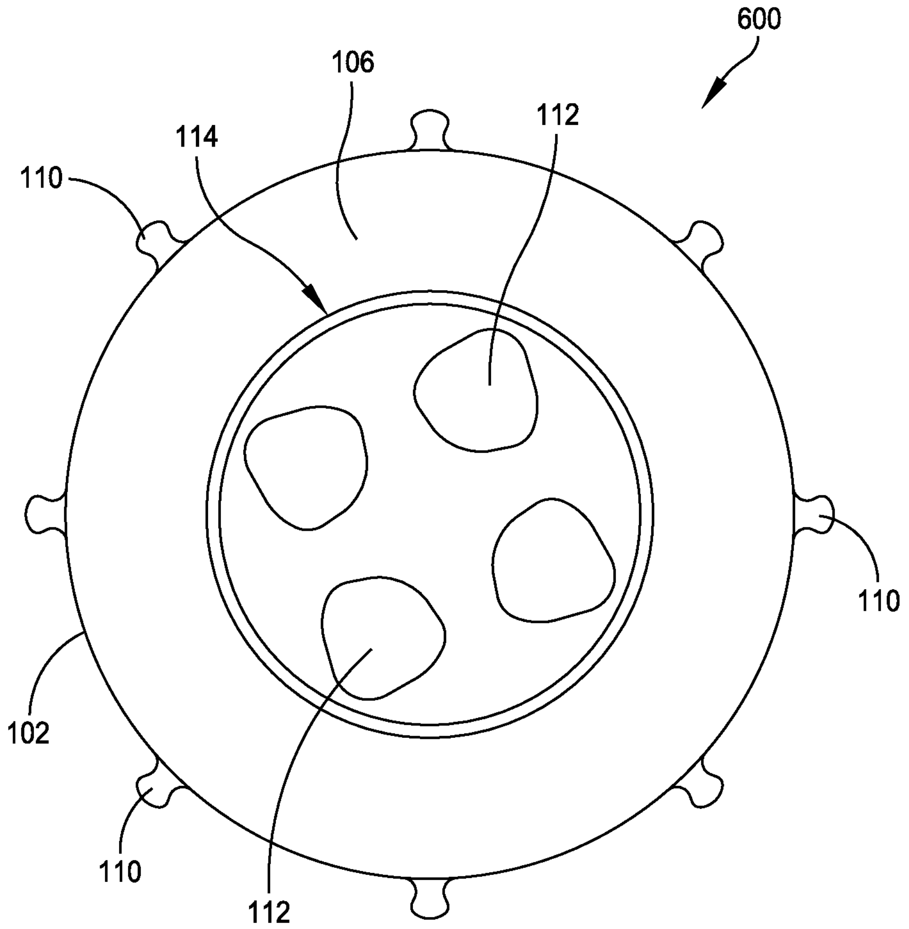
FIG. 30 is a bottom side view of the stem component illustrated in FIG. 27, in accordance with some embodiments.

FIGS. 27-31 illustrate another example of a stem component, in accordance with some embodiments. Stem component 600 may include a body 102 having a male coupling element 108 located at a first end 104 and a female engagement element 114 located at a second end 106. Male coupling element 108 may take the form of a threaded protrusion, as shown in FIGS. 27 and 28. Body 102 may include a plurality of anti-rotation features 110 extending along its length (e.g., between the first end 104 and second end 106). One or more engagement elements 112 may be disposed along a length of the body 102 with a respective engagement element 112 being disposed between adjacent anti-rotation features 110. As best seen in FIGS. 27 and 28, the engagement elements 112 may be arranged such that pairs of adjacent anti-rotation features 110 may alternatively have an engagement disposed therebetween, as opposed to each pair of adjacent anti-rotation features 110 having an engagement element 112 disposed therebetween, as shown in FIG. 1, for example. However, one of ordinary skill in the art will understand that one or more engagement elements 112 may be disposed between each of the adjacent pairs of anti-rotation features 110.

As best seen in FIG. 31, the female engagement element 114 may take the form of tapered hole 130 that extends inwardly from end 106. Here again, female engagement element 114 may take other forms, including a threaded hole, as will be understood by one of ordinary skill in the art. In some embodiments, stem component 600 may omit an engagement element 126, as shown in FIG. 31. However, stem component 600 may be configured with an engagement element 126 that is accessible via tapered hole 130. In some embodiments, the engagement element 126 may include a plurality of concentric ridges 128 as described above.

Stem component 600 may not include an engagement element 116 extending inwardly from end 106, but instead include an engagement element 132 that extends inwardly into the body adjacent to end 106. In some embodiments, engagement element 132 may include one or more flats 134 or other surfaces that are configured to be engaged by a tool, such as a wrench, for example, as best seen in FIGS. 27 and 28. The inward extension of engagement element 132 may form a flange that radially extends about the end 106, as best seen in FIGS. 27 and 28.

The stem components described herein may be coupled together in situ or ex situ when implanting a prosthesis stem. In some embodiments, for example, a prosthesis stem is implanted by first aligning an ankle joint and creating an intramedullary canal in a tibia, as described in U.S. Pat. No. 8,715,362. As noted above, although the process is described with respect to implanting a tibial stem, it should be understood that the stem may be implanted in other bones including, but not limited to, the femur, humerus, radius, fibula, and/or ulna, to list only a few possible examples.

A first stem component, which may be a top or superior stem component, may then be inserted into the intramedullary space. The top or superior stem component may include one or more engagement elements 112 disposed along its length. The one or more engagement elements 112 may be engaged by a first torquing instrument, which may have a complementary shape to the one or more engagement elements 112 such that the torquing instrument may be received within the one or more engagement elements 112.

A second stem component, which may be an intermediate and/or an inferior stem component, may be coupled to the first stem component by inserting the male coupling element 108 of the second stem component with the female coupling element 114 of the first stem component. In some embodiments, the coupling of the second stem component to the first stem component may include applying a torque to and rotating the second stem component relative to the first stem component. For example, the first torquing instrument may be inserted into one of the engagement elements 112 disposed along a length (or height) of the first stem component, and a second torquing instrument may be engaged with the engagement element 116 provided by the second end 106 of the second stem component. The second torquing instrument may be used to provide a torque to the second stem component while the first torquing instrument is used to hold the first stem component stationary. As described above, the interface between the second torquing instrument and the engagement element 116 of the second stem component may have a predetermined maximum torque value such that when a torque is applied that exceeds the predetermined maximum torque value the second torquing instrument will disengage from the engagement element 116. For example, the second torquing instrument may cam out of engagement with the engagement element 116 and/or the second torquing instrument may deform.

If the engagement element 116 is not accessible and/or a surgeon desired to provide additional torque to the second component, then another first torquing instrument may be used to engage one or more engagement elements 112 provided along a length of the second stem component. For example, the another first torquing instrument may be inserted into a first one of a plurality of engagement elements 112 to apply a first torque to the second stem component while the first torquing instrument is used to hold the first stem component stationary. The another first torquing instrument may be removed from its engagement with the first one of the plurality of engagement elements 112, and then placed in another one of the plurality of engagement elements 112 to provide a second torque to the second stem component. The process may be repeated until the desired amount of torque has been applied, as will be understood by one of ordinary skill in the art.

In some embodiments, one or more additional stem components may be coupled to the first and second components by repeating the steps described above. In some embodiments, the inferior stem component may include a female coupling element 116 in the form of a tapered hole 130 as shown in FIGS. 6, 11, 16, and 31.

A tray or other component of a prosthesis may be coupled to the stem. For example, a tray, which may include a protrusion extending from its superior surface, may be coupled to the inferior stem component by inserting the protrusion into the female coupling element 114, e.g., tapered hole 130. As described in U.S. Pat. No. 8,715,362, the tray may be configured to receive and/or otherwise support an articular surface, as will be understood by one of ordinary skill in the art.

The engagement elements 112 of the stem components described herein may also be used to remove a previously implanted stem. In some embodiments, removing a stem includes exposing at least a portion of a multi-component prosthesis stem that was previously implanted in a patient. For example, the exposure may be performed in accordance with the INBONE™ Total Ankle System Implant Removal Surgical Technique, available from Wright Medical Technology, Inc. As noted above, although the process is described with respect to removing a previously implanted tibial stem, it should be understood that the stem may have been implanted into bones other than a tibial including, but not limited to, the femur, humerus, radius, fibula, and/or ulna, to list only a few possible examples.

In some embodiments, after the tibial tray has been decoupled from the stem, a hole saw may be used to remove bone from around a circumference of the previously implanted stem.

With the stem exposed, a first torquing instrument may be placed into a first engagement element 112 of a plurality of engagement elements 112 provided along a length (or height) of a first stem component of a plurality of stem components of the multi-component stem. A first torque may be applied to the body 102 of the first stem component. In some embodiments, after the first torque is applied, the torquing instrument may be removed from the first engagement element 112 of the plurality of engagement elements 112. The torquing instrument may be inserted into a second engagement element 112 of a plurality of engagement elements 112, and then a second torque may be applied to the stem component. This process may be repeated until the stem component is removed from its engagement with the rest of the previously implanted stem prosthesis.

In some embodiments, additional leverage and/or manipulation of the stem component may be provided by inserting a removal tool through the female coupling element 114, which may include a hole, and into engagement with the engagement element 126 of the stem component. As described above, the engagement element 126 may include a plurality of concentric ridges 128 that are adapted to engage the removal tool. For example, one or more of the ridges 128 may bite into the removal tool as the removal tool is pulled distally and away from the remaining prosthesis stem. The process may be repeated until each of the stem components of the previously implanted multi-component stem is removed from the patient.

In some embodiments, an apparatus may include a body extending from a first end to a second end. The first end of the body may include a first coupling element, and the second end of the body may include a second coupling element. The second end of the body may include a first engagement element that extends inwardly into the body and may be disposed between a peripheral edge of the body and the second coupling element.

In some embodiments, the first coupling element may be a male coupling element, and the second coupling element may be a female coupling element. In some embodiments, the first coupling element may be a first male coupling element, and the second coupling element may be a second male coupling element. In some embodiments, the first coupling element may be a first female coupling element, and the second coupling element may be a second female coupling element. In some embodiments, the first coupling element may be a female coupling element, and the second coupling element may be a male coupling element.

In some embodiments, the body may define at least one second engagement element. The at least one second engagement element may be disposed along a length of the body such that the at least one second engagement element extends inwardly into the body between the first end and the second end.

In some embodiments, the at least one second engagement element may include a plurality of second engagement elements. Each second engagement element of the plurality of second engagement elements may be disposed at a respective location around the body.

In some embodiments, the body may be cylindrically shaped. The plurality of second engagement elements may be equidistantly located about a circumference of the body.

In some embodiments, the first engagement element may include a plurality of individual elements that may surround the second coupling element.

In some embodiments, each individual element of the plurality of individual elements may have a pyramidal shape.

In some embodiments, each individual element of the plurality of individual elements may have a shape of a frustum.

In some embodiments, the body may include a second engagement element. The second engagement element may be disposed in communication with the second coupling element and may include at least one ridge.

In some embodiments, the at least one ridge may include a plurality of ridges concentrically arranged about a longitudinal axis defined by the second coupling element.

In some embodiments, the first engagement element may be configured to be engaged by a tool for applying a torque. An interface between the first engagement element and the tool for applying the torque may be configured to transfer torque from the tool to the body up to a predetermined maximum value.

In some embodiments, the second coupling element may include a threaded hole.

In some embodiments, the second coupling element may include a tapered hole.

In some embodiments, a system may include a prosthesis stem including a plurality of stem components. At least one stem component of the plurality of stem components may include a body extending from a first end to a second end. A first coupling element may be disposed at the first end of the body, and a second coupling element may be disposed at the second end of the body. At least one first engagement element may be disposed along a length of the body such that the at least one first engagement element may be disposed between the first end and the second end. A second engagement element may extend inwardly into the second end of the body. The second engagement element may surround the second coupling element such that the second engagement element may be disposed between the second coupling element and a peripheral edge of the body.

In some embodiments, the first coupling element may be a male coupling element extending from the first end of the body, and the second coupling element may be a female coupling element extending inwardly from the second end of the body. In some embodiments, the first coupling element may be a first male coupling element extending from the first end of the body, and the second coupling element may be a second male coupling element extending from the second end of the body. In some embodiments, the first coupling element may be a first female coupling element extending inwardly from the first end of the body, and the second coupling element may be a second female coupling element extending inwardly from the second end of the body. In some embodiments, the first coupling element may be a female coupling element extending inwardly from the first end of the body, and the second coupling element may be a male coupling element extending from the second end of the body.

In some embodiments, the male coupling element may include a threaded protrusion, and the coupling element may include a threaded hole.

In some embodiments, the male coupling element may include a tapered protrusion, and the female coupling element may include a tapered hole.

In some embodiments, the at least one first engagement element may include a plurality of first engagement elements.

In some embodiments, the body may have a cylindrical shape. Each of the first engagement elements of the plurality of first engagement elements may be disposed at different location about a circumference of the body.

In some embodiments, each first engagement element of the plurality of first engagement elements may include a hole. The plurality of first engagement elements may be equidistantly spaced about the circumference of the body.

In some embodiments, the second engagement element may be configured to be engaged by a tool for applying a torque. An interface between the second engagement element and the tool for applying the torque may be configured to transfer torque from the tool to the body up to a predetermined maximum value.

In some embodiments, the body may include a third engagement element disposed in communication with the second coupling element. The third engagement element may include a plurality of ridges concentrically arranged about a longitudinal axis defined by the body.

In some embodiments, the second coupling element may include a tapered hole. A longitudinal axis defined by the tapered hole may be coaxial and/or collinear with the longitudinal axis defined by the body.

In some embodiments, a tray may be configured to be coupled to the prosthesis stem, and an articular surface may be configured to be coupled to the tray.

In some embodiments, the at least stem component may be formed using an additive manufacturing process.

In some embodiments, a system may include a prosthesis stem. The prosthesis stem may include a plurality of stem components. A first stem component of the plurality of stem components may include a first body extending from a first end to a second end. A first coupling element may be disposed at the first end of the first body. A second coupling element may be disposed at the second end of the first body. A first engagement element may be accessible via the second end of the first body and may be disposed between the first coupling element and the first end of the first body. In some embodiments, a second engagement element may extend inwardly into the second end of the first body. The second engagement element may surround the second coupling element such that the second engagement element may be disposed between the second coupling element and a peripheral edge of the first body.

In some embodiments, the first coupling element may be a male coupling element extending from the first end of the body, and the second coupling element may be a female coupling element extending inwardly from the second end of the body. In some embodiments, the first coupling element may be a first male coupling element extending from the first end of the body, and the second coupling element may be a second male coupling element extending from the second end of the body. In some embodiments, the first coupling element may be a first female coupling element extending inwardly from the first end of the body, and the second coupling element may be a second female coupling element extending inwardly from the second end of the body. In some embodiments, the first coupling element may be a female coupling element extending inwardly from the first end of the body, and the second coupling element may be a male coupling element extending from the second end of the body.

In some embodiments, the second coupling element may include a tapered hole. The first engagement element may include at least one ridge that is concentrically arrange with the tapered hole.

In some embodiments, the first coupling element may include a tapered protrusion.

In some embodiments, the first coupling element may include a threaded protrusion.

In some embodiments, a second stem component of the plurality of stem components may include a second body. A third coupling element may be disposed at a first end of the second body. A fourth coupling element may be disposed at the second end of the second body. A third engagement element may extend inwardly into the second end of the second body. The third engagement element may surround the fourth coupling element such that the third engagement element may be disposed between the fourth coupling element and a peripheral edge of the second body.

In some embodiments, the third coupling element may be a male coupling element extending from the first end of the second body, and the fourth coupling element may be a female coupling element extending inwardly from the second end of the second body. In some embodiments, the third coupling element may be a first male coupling element extending from the first end of the second body, and the fourth coupling element may be a second male coupling element extending from the second end of the second body. In some embodiments, the third coupling element may be a first female coupling element extending inwardly from the first end of the second body, and the fourth coupling element may be a second female coupling element extending inwardly from the second end of the second body. In some embodiments, the third coupling element may be a female coupling element extending inwardly from the first end of the second body, and the fourth coupling element may be a male coupling element extending from the second end of the second body.

In some embodiments, the first coupling element may include a threaded protrusion, the second coupling element may include a tapered hole, and fourth coupling element may include a threaded hole that is sized and configured to receive the first coupling element.

In some embodiments, a tray may include a tapered protrusion extending from an upper surface. The tapered protrusion may be sized and configured to be received in the second coupling element of the first body.

In some embodiments, a method may include engaging a first engagement element provided by a body of a first component and applying a torque to a body of a first component with the torquing instrument to couple the first component to a second component. The first engagement element may be disposed at a first end of the body of the first component and may extend inwardly into the body of the first component.

In some embodiments, a method may include inserting a male coupling element provided by a first component into a female coupling element provided by a second component, engaging a first engagement element with a torquing instrument, and applying a torque to a body of the first component with the torquing instrument to couple the first component to the second component. The first engagement element may be disposed at a first end of the body and may extend inwardly into the body of the first component.

In some embodiments, an interface may be provided by the first engagement element and the torquing instrument has a predetermined maximum torque value.

In some embodiments, the male coupling element may be provided by the first component and may include a threaded protrusion. The female coupling element may be provided by the second component and may include a threaded hole.

In some embodiments, the first component may be a first stem component of a multi-component prosthesis stem, the second component may be a second stem component of the multi-component prosthesis stem, and the first component may be coupled to the second component in situ.

In some embodiments, a method may include exposing at least a portion of a multi-component prosthesis stem that was previously implanted in a patient, inserting a torquing tool into a first engagement element of a plurality of engagement elements provided along a length of a first stem component of the multi-component prosthesis stem, and applying a first torque to a body of the first stem component of the multi-component stem to disengage a first coupling element of the first stem component from a first coupling element of a second component of the multi-component stem.

In some embodiments, after applying the first torque, the torquing tool may be removed from the first engagement element. The torquing tool may be inserted into a second engagement element of the plurality of engagement elements, and a second torque may be applied to the body of the first stem component of the multi-component stem.

In some embodiments, a tray may be decoupled from a second coupling element defined by the first stem component. A removal tool may be inserted through the second coupling element defined by the first stem component and into engagement with a third engagement element that is located within the first stem component. The first stem component may be removed from the patient.

Although the components, systems, kits, and methods have been described in terms of exemplary embodiments, they are not limited thereto. Rather, the appended claims should be construed broadly, to include other variants and embodiments of the components, systems, kits, and methods, which may be made by those skilled in the art without departing from the scope and range of equivalents.

What is claimed is:

1. An apparatus, comprising:

a body extending from a first end to a second end, the first end including a first coupling element, the second end including a second coupling element, the second end of the body including a first engagement element that extends inwardly into the body and is disposed between a peripheral edge of the body and the second coupling element, the first engagement element including a plurality of frustum-shaped depressions that extend inwardly into the second end and radiate about the second coupling element.

2. The apparatus of claim 1, wherein the body defines at least one second engagement element, the at least one second engagement element disposed along a length of the body such that the at least one second engagement element extends inwardly into the body between the first end and the second end.

3. The apparatus of claim 2, wherein the at least one second engagement element includes a plurality of second engagement elements, each second engagement element of the plurality of second engagement elements being disposed at a respective location around the body.

4. The apparatus of claim 3, wherein the body is cylindrically shaped, and wherein the plurality of second engagement elements are equidistantly located about a circumference of the body.

5. The apparatus of claim 1, wherein the first engagement element includes a plurality of individual elements that surround the second coupling element.

6. The apparatus of claim 5, wherein each of the plurality of individual elements has a frustum shape.

7. The apparatus of claim 1, wherein the body includes a second engagement element, the second engagement element disposed in communication with the second coupling element and includes at least one ridge.

8. The apparatus of claim 7, wherein the at least one ridge includes a plurality of ridges concentrically arranged about a longitudinal axis defined by the second coupling element.

9. The apparatus of claim 1, wherein the first engagement element is configured to be engaged by a tool for applying a torque, and wherein an interface between the first engagement element and the tool for applying the torque is configured to transfer torque from the tool to the body up to a predetermined maximum value.

10. The apparatus of claim 1, wherein the second coupling element includes a threaded hole.

11. The apparatus of claim 1, wherein the second coupling element includes a tapered hole.

12. A system, comprising:

a prosthesis stem including a plurality of stem components, at least one stem component of the plurality of stem components including:
- a body extending from a first end to a second end,
- a first coupling element disposed at the first end of the body,
- a second coupling element disposed at the second end of the body,
- at least one first engagement element disposed along a length of the body such that the at least one first engagement element is disposed between the first end and the second end, and
- a second engagement element extending inwardly into the second end of the body, the second engagement element surrounding the second coupling element such that the second engagement element is disposed between the second coupling element and a peripheral edge of the body, the second engagement element including a plurality of frustum-shaped depressions that extend inwardly into the second end of the body and radiate about the second coupling element.

13. The system of claim 12, wherein the first coupling element includes a threaded protrusion, and wherein the second coupling element includes a threaded hole.

14. The system of claim 12, wherein the first coupling element includes a tapered protrusion, and wherein the second coupling element includes a tapered hole.

15. The system of claim 12, wherein the at least one first engagement element includes a plurality of first engagement elements.

16. The system of claim 15, wherein the body has a cylindrical shape, and wherein each of the first engagement elements of the plurality of first engagement elements is disposed at different location about a circumference of the body.

17. The system of claim 16, wherein each first engagement element of the plurality of first engagement elements includes a hole, and wherein the plurality of first engagement elements are equidistantly spaced about the circumference of the body.

18. The system of claim 12, wherein the second engagement element is configured to be engaged by a tool for applying a torque, and wherein an interface between the second engagement element and the tool for applying the torque is configured to transfer torque from the tool to the body up to a predetermined maximum value.

19. The system of claim 18, wherein the body includes a third engagement element disposed in communication with the second coupling element, the third engagement element including a plurality of ridges concentrically arranged about a longitudinal axis defined by the body.

20. The system of claim 13, further comprising:
- a tray configured to be coupled to the prosthesis stem; and
- an articular surface configured to be coupled to the tray.

21. The system of claim 12, wherein the at least stem component is formed using an additive manufacturing process.

22. A system, comprising:

a prosthesis stem including a plurality of stem components, a first stem component of the plurality of stem components including:
- a first body extending from a first end to a second end,
- a first coupling element disposed at the first end of the first body,
- a second coupling element disposed at the second end of the first body,
- a first engagement element accessible via the second end of the first body and disposed between the second coupling element and the first end of the first body, the first engagement element including at least one ridge disposed in communication with the second coupling element, and
- a second engagement element extending inwardly into the second end of the first body, the second engagement element surrounding the second coupling element such that the second engagement element is disposed between the second coupling element and a peripheral edge of the first body.

23. The system of claim 22, wherein the first coupling element includes a threaded protrusion.

24. The system of claim 23, wherein a second stem component of the plurality of stem components includes:
- a second body,
- a third coupling element disposed at a first end of the second body,
- a fourth coupling element disposed at a second end of the second body,
- a third engagement element extending inwardly into the second end of the second body, the third engagement element surrounding the fourth coupling element such that the third engagement element is disposed between the fourth coupling element and a peripheral edge of the second body.

25. The system of claim 24, further comprising a tray, the tray including a tapered protrusion extending from an upper surface, the tapered protrusion sized and configured to be received in the second coupling element of the first body.

26. The system of claim 24, wherein the second engagement element comprises a plurality of frustum-shaped depressions arranged circumferentially about the second coupling element.

27. The system of claim 26, wherein each frustum-shaped depression includes a planar inner bottom surface and sidewalls extending substantially perpendicularly from the planar inner bottom surface.

28. The system of claim 24, wherein the first body further includes a third engagement element disposed in communication with the second coupling element, the third engagement element comprising a plurality of ridges concentrically arranged about a longitudinal axis of the second coupling element.

29. The system of claim 28, wherein the plurality of ridges are angled toward the first end of the first body to resist disengagement of a removal tool inserted therethrough.

30. The system of claim 28, wherein the third engagement element is accessible via the second coupling element and is at least partially disposed between a superior-most portion of the second coupling element and the first end of the first body.

31. The system of claim 24, wherein the first body is cylindrical and includes a plurality of first engagement elements disposed around a circumference of the first body between the first end of the first body and the second end of the first body.

32. The system of claim 31, wherein the plurality of first engagement elements comprise through-holes that are substantially equidistantly spaced about the circumference of the first body.

33. The system of claim 24, wherein an interface between the second engagement element and a torquing tool is configured to transfer torque to the first body up to a predetermined maximum torque value.

34. The system of claim 24, wherein the second body includes the third coupling element and the fourth coupling element configured to releasably couple the second body to the first body.

35. The system of claim 34, wherein the third coupling element comprises a male protrusion configured to be received in the second coupling element of the first body and the fourth coupling element comprises a mating female receptacle sized and configured to receive a male coupling element of an adjacent stem component the male protrusion.

36. The system of claim 24, further comprising a tray configured to be coupled to the first body and an articular surface configured to be coupled to the tray.

* * * * *